*(12)* United States Patent
Tada et al.

US007201976B2

(10) Patent No.: US 7,201,976 B2
(45) Date of Patent: Apr. 10, 2007

(54) ORGANIC ELECTROLUMINESCENCE MATERIAL AND ELECTROLUMINESCENCE DEVICE USING THE SAME

(75) Inventors: Hiroshi Tada, Tokyo (JP); Atsushi Oda, Tokyo (JP); Hitoshi Ishikawa, Tokyo (JP); Satoru Toguchi, Tokyo (JP); Yukiko Morioka, Tokyo (JP)

(73) Assignee: Samsung SDI Co., Ltd., Suwon-si (KR)

( * ) Notice: Subject to any disclaimer, the term of this patent is extended or adjusted under 35 U.S.C. 154(b) by 0 days.

(21) Appl. No.: 10/448,704

(22) Filed: May 30, 2003

(65) Prior Publication Data

US 2004/0018387 A1    Jan. 29, 2004

Related U.S. Application Data

(63) Continuation of application No. 09/630,633, filed on Aug. 1, 2000, now abandoned.

(30) Foreign Application Priority Data

Aug. 2, 1999  (JP) .................................. 11-218336
Aug. 2, 1999  (JP) .................................. 11-218337

(51) Int. Cl.
*H01L 51/54* (2006.01)
*C07C 211/00* (2006.01)
*C09K 11/06* (2006.01)
*H05B 33/12* (2006.01)

(52) U.S. Cl. ...................... 428/690; 428/917; 313/504; 313/506; 257/40; 257/E51.051; 252/301.16; 252/301.35; 564/434

(58) Field of Classification Search ................ 428/690, 428/704, 917; 313/504, 506; 257/40, 103; 252/301.16; 564/426, 427, 428, 429, 433, 564/434

See application file for complete search history.

(56) References Cited

U.S. PATENT DOCUMENTS 5,998,046 A    12/1999  Tada et al. ................... 428/690

FOREIGN PATENT DOCUMENTS

| JP | 3-96961 | 4/1991 |
|---|---|---|
| JP | 7-20644 | 1/1995 |
| JP | 7-173113 | 7/1995 |
| JP | 7-175238 | 7/1995 |
| JP | 9-292724 | 11/1997 |
| JP | 9-304952 | 11/1997 |
| JP | 10-140146 | 5/1998 |
| JP | 11-102784 | 4/1999 |

*Primary Examiner*—Marie Yamnitzky
(74) *Attorney, Agent, or Firm*—H.C. Park & Associates, PLC

(57) ABSTRACT

An organic electroluminescence material of the present invention includes, in order to provide an durable organic EL device emitting light of high brightness, a compound shown by the general formula (A-I) or (B-I) (as explained in the specification) wherein, $A_1$ to $A_3$ which may be the same or different, are independently each a substituent shown by the general formula (A-II) (as explained in the specification): and $a_1$, $b_1$, and $b_2$ are independently each an aryl group which may be substituted, $a_1$ having at least one substituent shown by the general formula (B-II) (as explained in the specification), and $b_1$ and $b_2$ each having at least one substituent shown by the general formula (B-III) (as explained in the specification), and $b_1$ and $b_2$ may be the same of different.

14 Claims, 3 Drawing Sheets

Emission

Emission

Emission

Emission

Emission

Emission

ORGANIC ELECTROLUMINESCENCE MATERIAL AND ELECTROLUMINESCENCE DEVICE USING THE SAME

RELATED APPLICATION

The present application is a continuation of application, U.S. Ser. No. 09/630,633, filed on Aug. 1, 2000 now abandoned.

BACKGROUND OF THE INVENTION

The present invention relates to an organic-electroluminescence (EL) device used for planar light sources and displays, and the organic EL material therefor.

DESCRIPTION OF THE RELATED ART

An organic EL device has been attracting attention as a planar display element. The organic EL device with two or more organic layers has much improved light-emitting efficiency, emitting light of high brightness at a voltage of 10 V or less applied thereto (Applied Physics Letters, vol. 51, pp. 913, 1987 and vol. 56, pp. 799, 1990). It generally comprises an anode, hole transport region, EL light-emitting region, electron transport region and cathode as the basic structure. It may lack one of the hole and electron transport regions, or both. Each region may consist of one layer, or two or more layers.

Many of the conventional organic EL devices use a triphenylamine derivatives for the hole transport region. For example, 1,1-bis-(4-diparatolylaminophenyl)cyclohexane and N,N'-diphenyl-N,N'-bis(3-methylphenyl)-1,1'-biphenyl-4,4'-diamine are preferably used, because of their good hole injection and film-making characteristics. It is reported, however, that the films of these compounds are uniform immediately after they are formed, but tend to suffer agglomeration in several days (Spring Meeting of the Japan Society of Applied Physics, 30a-SZK-1, 1993, Autumn Meeting of the Japan Society of Applied Physics, 29a-ZC-8, 1993), accelerating deterioration of brightness (Applied Physics Letters, vol. 68, pp. 1787, 1996).

On the other hand, Japanese Patent Publication No. SHO 64-7635 discloses use of a porphyrin compound for the hole transport layer. However, crystallization or agglomeration of the layer also occurs after the device is assembled, deteriorating its functions.

Japanese Patent Publication No. HEI 7-110940 (110940/1995 B) and Applied Physics Letters, vol. 65, pp. 807, 1994 disclose use of a starburst type tertiary amine derivatives for the hole transport material. However, it also fails to give the device which can continuously emit sufficiently bright light.

Japanese Patent No. 2597377 discloses an organic-EL device structure comprising two hole transport layers of hole injection type compounds, one being of a porphyrin compound and the other of an aromatic tertiary amine from the anode side, in order to reduce pinholes and thereby to improve device stability. However, even this structure shows insufficient improvement in device stability.

Moreover, the conventional organic EL device is insufficient in brightness, when it is to be used for light-emitting devices, e.g., full-color display, and is required to have higher brightness.

As described above, the organic EL device is less durable than other types of light-emitting devices, and insufficient in brightness-related properties, which have greatly retarded its commercialization.

The present invention has been developed to solve the above problems, and thereby to provide an organic EL device of longer serviceability and emitting light of high brightness.

SUMMARY OF THE INVENTION

The organic electroluminescence material, characterized by containing a compound shown by the following general formula (A-I):

(A-I)

wherein, $A_1$ to $A_3$ are independently, each a substituent shown by the general formula (A-II). which may be the same or different.

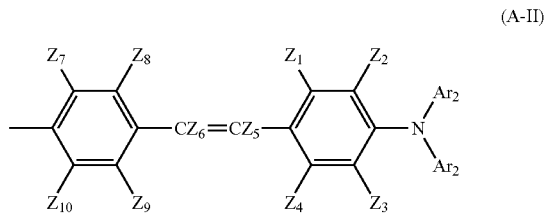

(A-II)

wherein, at least one of $Z_1$ to $Z_4$ and $Z_7$ to $Z_{10}$ are independently, each a halogen atom or hydroxyl, amino or substituted amino, nitro, cyano, alkyl or substituted alkyl, alkenyl or substituted alkenyl (except styryl), cycloalkyl or substituted cycloalkyl, alkoxy or substituted alkoxy, aromatic hydrocarbon or substituted aromatic hydrocarbon, aromatic heterocyclic or substituted aromatic heterocyclic, aralkyl or substituted aralkyl, aryloxy or substituted aryloxy, alkoxy carbonyl or substituted alkoxy carbonyl or carboxyl group, and the others being a hydrogen atom;

$Z_1$ and $Z_2$, $Z_3$ and $Z_4$ and $Z_7$ to $Z_{10}$ may form a ring by two adjacent atoms or groups;

$Z_5$ and $Z_6$ are independently, each a hydrogen atom, alkyl or substituted alkyl, aromatic hydrocarbon or substituted aromatic hydrocarbon, or aromatic heterocyclic or substituted aromatic heterocyclic group; and $Ar_1$ and $Ar_2$ are independently each an aryl group which may be substituted.

The organic electroluminescence material, characterized by containing a compound shown by the following general formula (A-III) (Except that the substituent shown by the general formula (A-V) is at the site of $Y_3$ and, at the same time, the substituent shown by the formula —$NAr_1Ar_2$ is at the site of $Y_8$.):

(A-III)

wherein, $B_1$ to $B_3$ are independently, each a substituent shown by the general formula (A-IV). which may be the same or different.

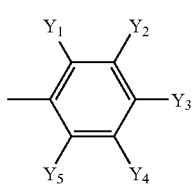

(A-IV)

wherein, at least one of $Y_1$ to $Y_5$ is a substituent shown by the general formula (A-V), the others being independently each a hydrogen atom, a halogen atom, or hydroxyl, amino or substituted amino, nitro, cyano, alkyl or substituted alkyl, alkenyl or substituted alkenyl (other than styryl), cycloalkyl or substituted cycloalkyl, alkoxy or substituted alkoxy, aromatic hydrocarbon or substituted aromatic hydrocarbon, aromatic heterocyclic or substituted aromatic heterocyclic, aralkyl or substituted aralkyl, aryloxy or substituted aryloxy, alkoxy carbonyl or substituted alkoxy carbonyl or carboxyl group; and $Y_1$ to $Y_5$ may form a ring by two adjacent atoms or groups;

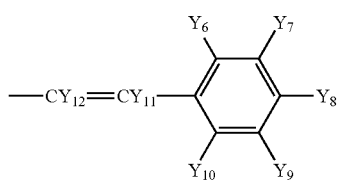

(A-V)

wherein, at least one of $Y_6$ to $Y_{10}$ is a substituent shown by the formula $-NAr_1Ar_2$, the others being independently each a hydrogen atom, a halogen atom or hydroxyl, amino or substituted amino, nitro, cyano, alkyl or substituted alkyl, alkenyl or substituted alkenyl (other than styryl), cycloalkyl or substituted cycloalkyl, alkoxy or substituted alkoxy, aromatic hydrocarbon or substituted aromatic hydrocarbon, aromatic heterocyclic or substituted aromatic heterocyclic, aralkyl or substituted aralkyl, aryloxy or substituted aryloxy, alkoxy carbonyl or substituted alkoxy carbonyl or carboxyl group;

$Y_6$ to $Y_{10}$ may form a ring by two adjacent atoms or groups;

$Ar_1$ and $Ar_2$ are independently each an aryl group which may be substituted; and $Y_{11}$ and $Y_{12}$ are independently, each a hydrogen atom or alkyl or substituted alkyl, aromatic hydrocarbon or substituted aromatic hydrocarbon, aromatic heterocyclic or substituted aromatic heterocyclic group.

The organic electroluminescence material, characterized by containing a compound shown by the following general formula (A-VI):

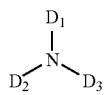

(A-VI)

wherein, $D_1$ to $D_3$ are independently, each a substituent shown by the general formula (A-VII). They may be the same or different.

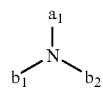

(A-VII)

wherein, at least one of $X_1$ to $X_5$ is a substituent shown by the formula $-NAr_1Ar_2$, the others being independently each a hydrogen atom, a halogen atom or hydroxyl, amino or substituted amino, nitro, cyano, alkyl or substituted alkyl, alkenyl or substituted alkenyl (other than styryl), cycloalkyl or substituted cycloalkyl, alkoxy or substituted alkoxy, aromatic hydrocarbon or substituted aromatic hydrocarbon, aromatic heterocyclic or substituted aromatic heterocyclic, aralkyl or substituted aralkyl, aryloxy or substituted aryloxy, alkoxy carbonyl or substituted alkoxy carbonyl or carboxyl group;

$Z_1$ to $Z_5$ may form a ring by two adjacent atoms or groups;

$Ar_1$ and $Ar_2$ are independently, each an aryl group which may be substituted;

One of $X_6$ and $X_7$ is hydrogen, an alkyl group having two or more carbons, an aromatic hydrocarbon group or aromatic heterocyclic group all of which may be substituted and the other is an alkyl group having 2 or more carbons, aromatic hydrocarbon group or aromatic heterocyclic group, all of which may be substituted; and $X_8$ to $X_{11}$ are independently, each a hydrogen atom, a halogen atom or hydroxyl, amino or substituted amino, nitro, cyano, alkyl or substituted alkyl, alkenyl or substituted alkenyl (except styryl), cycloalkyl or substituted cycloalkyl, alkoxy or substituted alkoxy, aromatic hydrocarbon or substituted aromatic hydrocarbon, aromatic heterocyclic or substituted aromatic heterocyclic, aralkyl or substituted aralkyl, aryloxy or substituted aryloxy, alkoxy carbonyl or substituted alkoxy carbonyl carboxyl group and $X_8$ to $X_{11}$ may form a ring by two adjacent atoms or groups.

The organic electroluminescence material, characterized by containing a compound shown by the following general formula (B-I):

(B-I)

$$\underset{b_1 \quad b_2}{\overset{a_1}{N}}$$

wherein, $a_1$, $b_1$ and $b_2$ are independently, each an aryl group which may be substituted, $a_1$ having at least one substituent shown by the general formula (B-II), each of $b_1$ and $b_2$ having at least one substituent shown by the general formula (B-III), and $b_1$ and $b_2$ may be the same or different:

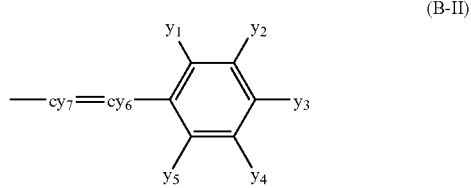

(B-II)

wherein, $y_1$ to $y_5$ are independently, each a hydrogen atom, a halogen atom or hydroxyl, nitro, cyano, alkyl or substituted alkyl, alkenyl or substituted alkenyl (except styryl), cycloalkyl or substituted cycloalkyl, alkoxy or substituted alkoxy, aromatic hydrocarbon or substituted aromatic hydrocarbon, aromatic heterocyclic or substituted aromatic heterocyclic, aralkyl or substituted aralkyl, aryloxy or substituted aryloxy, alkoxy carbonyl or substituted alkoxy carbonyl or carboxyl group; and $y_1$ to $y_5$ may form a ring by two adjacent atoms or groups;

$y_6$ and $y_7$ are independently, each a hydrogen atom, alkyl or substituted alkyl, aromatic hydrocarbon or substituted aromatic hydrocarbon, or aromatic heterocyclic or substituted aromatic heterocyclic group.

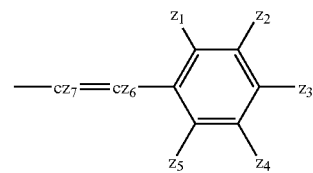

(B-III)

wherein, at least one of $z_1$ to $z_5$ is a substituent shown by the formula —$NAr_1Ar_2$, the others being independently, each a hydrogen atom, a halogen atom or hydroxyl, amino or substituted amino, nitro, cyano, alkyl or substituted alkyl, alkenyl or substituted alkenyl (except styryl), cycloalkyl or substituted cycloalkyl, alkoxy or substituted alkoxy, aromatic hydrocarbon or substituted aromatic hydrocarbon, aromatic heterocyclic or substituted aromatic heterocyclic, aralkyl or substituted aralkyl, aryloxy or substituted aryloxy, alkoxy carbonyl or substituted alkoxy carbonyl or carboxyl group;

$z_1$ to $z_4$ may form a ring by two adjacent atoms or groups;

$Ar_1$ and $Ar_2$ are independently, each an aryl group which may be substituted; and $z_6$ and $z_7$ are independently, each a hydrogen atom or alkyl or substituted alkyl, aromatic hydrocarbon or substituted aromatic hydrocarbon, or aromatic heterocyclic or substituted aromatic heterocyclic group.

In the present invention, it is preferable that organic electroluminescence material, wherein at least one material of said organic electroluminescence materials according to any one of claims 1 to 4, is dispersed in a polymer binder.

In the organic electroluminescence device comprising one or more layers of organic thin films put between the anode and cathode, wherein at least one of said layers is composed of at least one of the organic electroluminescence materials according to any one of claims 1 to 4.

In the organic electroluminescence device of claim 6, wherein at least one of said layers is composed of at least one of the organic electroluminescence materials according to any one of claims 1 to 4, and 2 to 500 nm thick.

It is preferable that the organic electroluminescence device of claims 6 to 7, wherein one of its hole transport, light-emitting and electron transport layers is composed of at least one of the organic electroluminescence materials according to any one of claims 1 to 4.

It is also preferable that the organic electroluminescence device of claim 6 or claim 8, wherein said light-emitting layer is doped with an organic luminescent agent as the dopant.

It is also preferable that the organic electroluminescence device of claim 6, wherein said hole transport layer contains a first and second hole transport layer facing the anode and light-emitting layer sides, respectively, and said first hole transport layer is composed of at least one of the organic electroluminescence materials according to any one of claims 1 to 4.

A preferred embodiment of the present invention is the organic electroluminescence device described in claim 10, wherein said second hole transport layer contains an aromatic tertiary amine.

Another preferred embodiment of the present invention is the organic electroluminescence device described in claims 8, 10 and 11, wherein an anode interface layer is provided between the anode and the first hole transport layer.

BRIEF DESCRIPTION OF THE DRAWINGS

The objects and features of the present invention will become more apparent from the consideration of the following detailed description taken in conjunction with the accompanying drawings, in which.

DESCRIPTION OF THE PREFERRED EMBODIMENTS

Figure 1A:
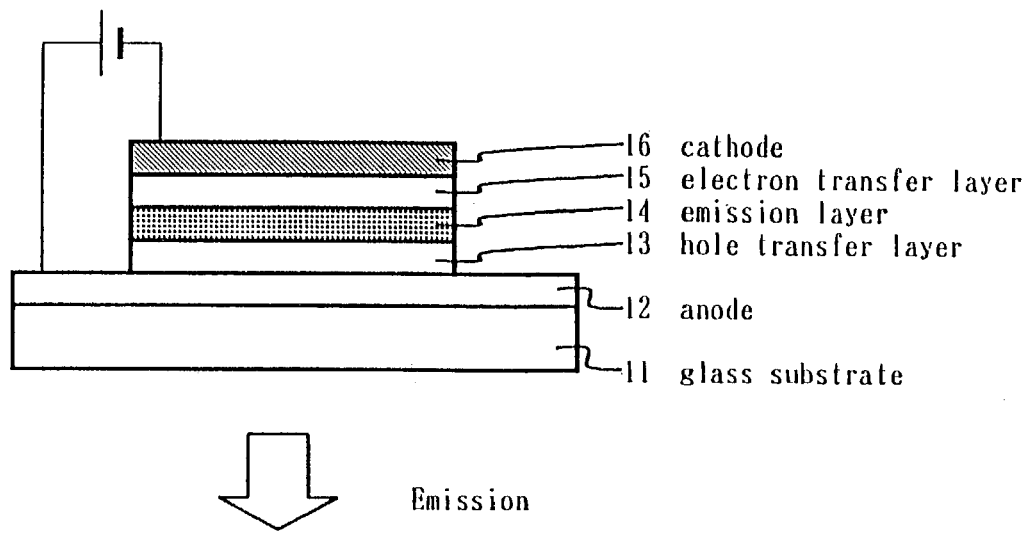
FIG. 1A and FIG. 1B show an example of the sectional view of the organic EL device of the present invention.

Preferred embodiments of the present invention will be described. FIG. 1(a) shows a section of an organic EL device which uses an organic EL material of the present invention, where reference numeral 11 denotes a glass substrate; reference numeral 12 denotes an anode; reference numeral 13 denotes a hole transport layer; reference numeral 14 denotes a light-emitting layer; reference numeral 15 denotes an electron transport layer; and reference numeral 16 denotes a cathode. The organic EL material of the present invention is used at least one of the hole transport layer 13, light-emitting layer 14, and electron transport layer 15.

Figure 1B:
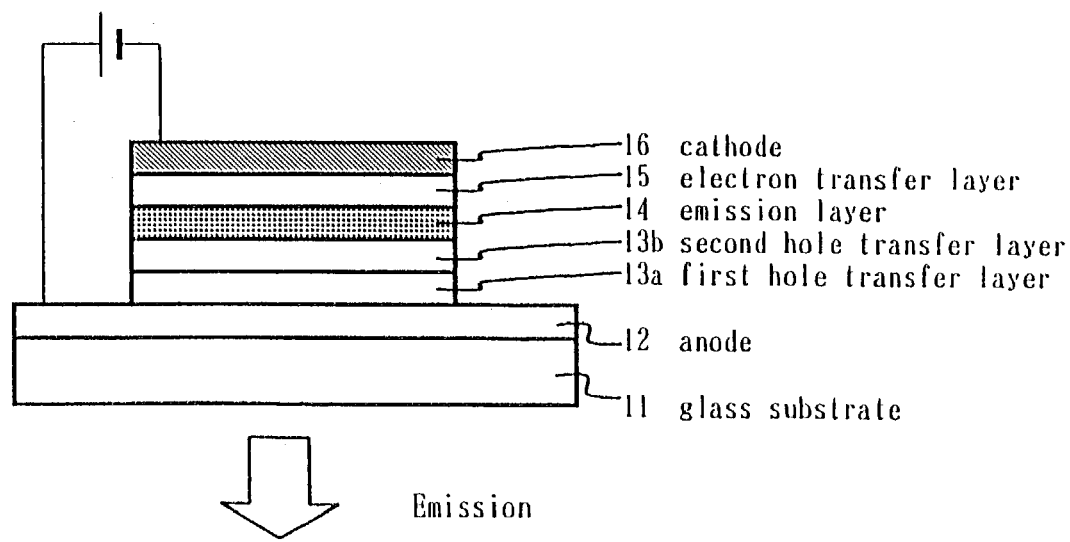

The organic EL device of the present invention may dispense with the hole transport layer 13 and/or electron transport layer 15. FIG. 2 (a) shows the device which dispenses with the electron transport layer 15, and FIG. 3 shows the device which dispenses with both layers. The hole transport layer 13 may be divided into the first hole transport layer 13a on the anodic side and second hole transport layer 13b on the light-emitting device side, as shown in FIGS. 1(b) and 2(b), where the former is made of the organic EL material of the present invention and the latter of a known organic material.

Figure 4:
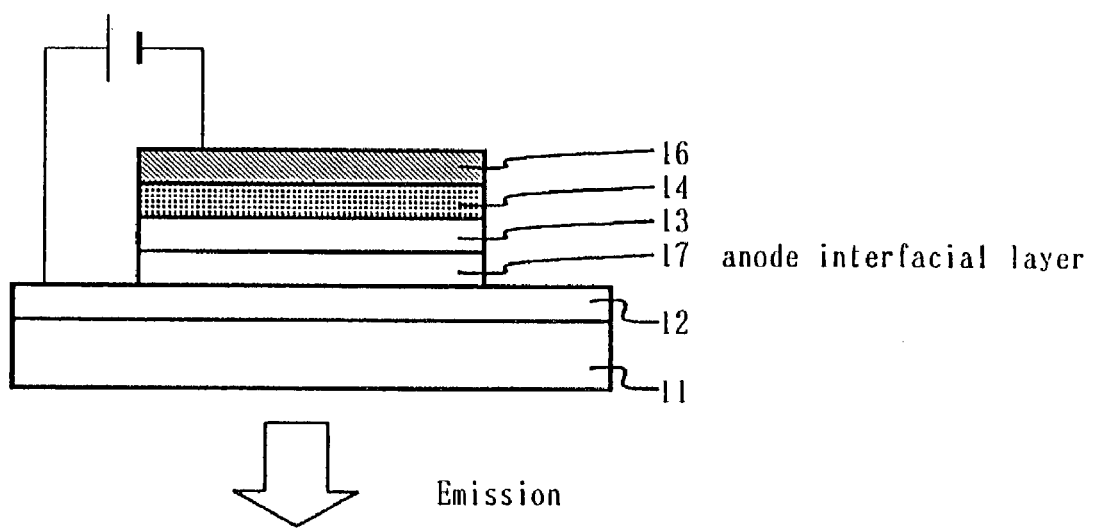
FIG. 4 shows still another example of the sectional view of the organic EL device of the present invention.

An anode interface layer may be provided between the anode 12 and hole transport layer 13, or anode 12 and first hole transport layer 13a. FIG. 4 shows an example of the anode interface layer provided between the anode 12 and hole transport layer 13 for the organic EL device, shown in FIG. 2(a).

The halogen atoms for the substituents shown by the general formula (A-II), (A-IV), (A-V), (A-VII), (B-II) or (B-III) include fluorine, chlorine, bromine and iodine.

The amino group or substituted amino group, is shown bfy the general formula —$NX^1X^2$, wherein $X^1$ and $X^2$ are independently, each hydrogen atom or methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl, phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 4-styrylphenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naththyl, 4-methyl-1-naththyl, 4-methyl-1-anthryl, 4'-methylbiphenylyl, 4"-t-butyl-p-terphenyl-4-yl, 2-pyrrolyl, 3-pyrrolyl, pyrazinyl, 2-pyridinyl, 3-pyridinyl, 4-pyridinyl, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthrolin-2-yl, 1,7-phenanthrolin-3-yl, 1,7-phenanthrolin-4-yl, 1,7-phenanthrolin-5-yl, 1,7-phenanthrolin-6-yl, 1,7-phenanthrolin-8-yl, 1,7-phenanthrolin-9-yl, 1,7-phenanthrolin-10-yl, 1,8-phenanthrolin-2-yl, 1,8-phenanthrolin-3-yl, 1,8-phenanthrolin-4-yl, 1,8-phenanthrolin-5-yl, 1,8-phenanthrolin-6-yl, 1,8-phenanthrolin-7-yl, 1,8-phenanthrolin-9-yl, 1,8-phenanthrolin-10-yl, 1,9-phenanthrolin-2-yl, 1,9-phenanthrolin-3-yl, 1,9-phenanthrolin-4-yl, 1,9-phenanthrolin-5-yl, 1,9-phenanthrolin-6-yl, 1,9-phenanthrolin-7-yl, 1,9-phenanthrolin-8-yl, 1,9-phenanthrolin-10-yl, 1,10-phenanthrolin-2-yl, 1,10-phenanthrolin-3-yl, 1,10-phenanthrolin-4-yl, 1,10-phenanthrolin-5-yl, 2,1-phenanthrolin-1-yl, 2,9-phenanthrolin-3-yl, 2,9-phenanthrolin-4-yl, 2,9-phenanthrolin-5-yl, 2,9-phenanthrolin-6-yl, 2,9-phenanthrolin-7-yl, 2,9-phenanthrolin-8-yl, 2,9-phenanthrolin-10-yl, 2,8-phenanthrolin-71-yl, 2,8-phenanthrolin-3-yl, 2,8-phenanthrolin-4-yl, 2,8-phenanthrolin-5-yl, 2,8-phenanthrolin-6-yl, 2,8-phenanthrolin-7-yl, 2,8-phenanthrolin-9-yl, 2,8-phenanthrolin-10-yl, 2,7-phenanthrolin-1-yl, 2,7-phenanthrolin-3-yl, 2,7-phenanthrolin-4-yl, 2,7-phenanthrolin-5-yl, 2,7-phenanthrolin-6-yl, 2,7-phenanthrolin-8-yl, 2,7-phenanthrolin-9-yl, 2,7-phenanthrolin-10-yl, 1-phenazinyl, 2-phenazinyl, 1-phenothiazinyl, 2-phenothiazinyl, 3-phenothiazinyl, 4-phenothiaznyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, and 4-t-butyl-3-indolyl group.

The alkyl or substituted alkyl group, useful for the present invention include(s) methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, and 1,2,3-trinitropropyl group.

The alkenyl or substituted alkenyl group, useful for the present invention includes vinyl, allyl, 1-butenyl, 2-butenyl, 3-butenyl, 1,3-butanedienyl, 1-methylvinyl, 1-methylallyl, 1,1-dimethylallyl, 2-methylallyl, 1-phenylallyl, 2-phenylallyl, 3-phenylallyl, 3,3-diphenylallyl, 1,2-dimethylallyl, 1-phenyl-1-butenyl, and 3-phenyl-1-butenyl. The cycloalkyl or substituted cycloalkyl group, useful for the present invention include cyclopropyl, cyclobutyl, cyclopentyl, cyclohexyl, and 4-methylcyclohexyl group.

The alkoxy or substituted alkoxy group, is represented by the general formula —OY. The groups represented by Y useful for the present invention include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichlioropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, and 1,2,3-trinitropropyl.

The aromatic hydrocarbon or substituted aromatic hydrocarbon group(s), useful for the present invention includes phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naththyl, 4-methyl-1-naththyl, 4-methyl-1-anthryl, 4'-methylbiphenylyl, and 4"-t-butyl-p-terphenyl-4-yl group.

The aromatic heterocyclic or substituted aromatic heterocyclic group(s), useful for the present invention include 1-pyrrolyl, 2-pyrrolyl, 3-pyrrolyl, pyrazinyl, 2-pyridinyl, 3-pyridinyl, 4.-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthrolin-2-yl, 1,7-phenanthrolin-3-yl, 1,7-phenanthrolin-4-yl, 1,7-phenanthrolin-5-yl, 1,7-phenanthrolin-6-yl, 1,7-phenanthrolin-8-yl, 1,7-phenanthrolin-9-yl, 1,7-phenanthrolin-10-yl, 1,8-phenanthrolin-2-yl, 1,8-phenanthrolin-3-yl, 1,8-phenanthrolin-4-yl, 1,8-phenanthrolin-5-yl, 1,8-phenanthrolin-6-yl, 1,8-phenanthrolin-7-yl, 1,8-phenanthrolin-9-yl, 1,8-phenanthrolin-10-yl, 1,9-phenanthrolin-2-yl, 1,9-phenanthrolin-3-yl, 1,9-phenanthrolin-4-yl, 1,9-phenanthrolin-5-yl, 1,9-phenanthrolin-6-yl, 1,9-phenanthrolin-7-yl, 1,9-phenanthrolin-8-yl, 1,9-phenanthrolin-10-yl, 1,10-phenanthrolin-2-yl, 1,10-phenanthrolin-3-yl, 1,10-phenanthrolin-4-yl, 1,10-phenanthrolin-5-yl, 2,9-phenanthrolin-1-yl, 2,9-phenanthrolin-3-yl, 2,9-phenanthrolin-4-yl, 2,9-phenanthrolin-5-yl, 2,9-phenanthrolin-6-yl, 2,9-phenanthrolin-7-yl, 2,9-phenanthrolin-8-yl, 2,9-phenanthrolin-10-yl, 2,8-phenanthrolin-1-yl, 2,8-phenanthrolin-3-yl, 2,8-phenanthrolin-4-yl, 2,8-phenanthrolin-5-yl, 2,8-phenanthrolin-6-yl, 2,8-phenanthrolin-7-yl, 2,8-phenanthrolin-9-yl, 2,8-phenanthrolin-10-yl, 2,7-phenanthrolin-1-yl, 2,7-phenanthrolin-3-yl, 2,7-phenanthrolin-4-yl, 2,7-phenanthrolin-5-yl, 2,7-phenanthrolin-6-yl, 2,7-phenanthrolin-8-yl, 2,7-phenanthrolin-9-yl, 2,7-phenanthrolin-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, and 4-t-butyl-3-indolyl group.

The aralkyl or substituted aralkyl group(s), useful for the present invention include(s) benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, and 1-chloro-2-phenylisopropyl.

The aryloxy or substituted aryloxy group(s), which may be substituted, is represented by the general formula —OZ. The groups represented by Z useful for the present invention include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naththyl, 4-methyl-1-naththyl, 4-methyl-1-anthryl, 4'-methylbiphenylyl, 4"-t-butyl-p-terphenyl-4-yl, 2-pyrrolyl, 3-pyrrolyl, pyrazinyl, 2-pyridinyl, 3-pyridinyl, 4-pyridinyl, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthrolin-2-yl, 1,7-phenanthrolin-3-yl, 1,7-phenanthrolin-4-yl, 1,7-phenanthrolin-5-yl, 1,7-phenanthrolin-6-yl, 1,7-phenanthrolin-8-yl, 1,7-phenanthrolin-9-yl, 1,7-phenanthrolin-10-yl, 1,8-phenanthrolin-2-yl, 1,8-phenanthrolin-3-yl, 1,8-phenanthrolin-4-yl, 1,8-phenanthrolin-5-yl, 1,8-phenanthrolin-6-yl, 1,8-phenanthrolin-7-yl, 1,8-phenanthrolin-9-yl, 1,8-phenanthrolin-10-yl, 1,9-phenanthrolin-2-yl, 1,9-phenanthrolin-3-yl, 1,9-phenanthrolin-4-yl, 1,9-phenanthrolin-5-yl, 1,9-phenanthrolin-6-yl, 1,9-phenanthrolin-7-yl, 1,9-phenanthrolin-8-yl, 1,9-phenanthrolin-10-yl, 1,10-phenanthrolin-2-yl, 1,10-phenanthrolin-3-yl, 1,10-phenanthrolin-4-yl, 1,10-phenanthrolin-5-yl, 2,9-phenanthrolin-1-yl, 2,9-phenanthrolin-3-yl, 2,9-phenanthrolin-4-yl, 2,9-phenanthrolin-5-yl, 2,9-phenanthrolin-6-yl, 2,9-phenanthrolin-7-yl, 2,9-phenanthrolin-8-yl, 2,9-phenanthrolin-10-yl, 2,8-phenanthrolin-1-yl, 2,8-phenanthrolin-3-yl, 2,8- phenanthrolin-4-yl, 2,8-phenanthrolin-5-yl, 2,8-phenantholin-6-yl, 2,8-phenanthrolin-7-yl, 2,8-phenanthrolin-9-yl, 2,8-phenanthrolin-10-yl, 2,7-phenanthrolin-1-yl, 2,7-phenanthrolin-3-yl, 2,7-phenanthrolin-4-yl, 2,7-phenanthrolin-5-yl, 2,7-phenanthrolin-6-yl, 2,7-phenanthrolin-8-yl, 2,7-phenanthrolin-9-yl, 2,7-phenanthrolin-10-yl, 1-phenazinyl, 2-phenazinyl, 1-phenothiazinyl, 2-phenothiazinyl, 3-phenothiazinyl, 4-phenothiazinyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, and 4-t-butyl-3-indolyl group.

The alkoxy carbonyl or substituted alkoxy carbonyl group(s), is represented by the general formula —COOY. The groups represented by Y useful for the present invention include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, -1,2-diiodoethyl, -1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, and 1,2,3-trinitropropyl group.

The divalent groups which can form a ring include tetramethylene, pentamethylene, hexamethylene, diphenylmethane-2,2'-diyl, diphenylethane-3,3'-diyl, diphenylpropane-4,4'-diyl, and 1,3-butadiene-1,4-diyl.

The aryl groups represented by $a_1$, $b_1$, $b_2$, $Ar_1$ and $Ar_2$ include phenyl, naphthyl, anthryl, phenanthryl, naphthacenyl and pyrenyl.

These aryl group(s) may be substituted with a halogen atom, hydroxyl, the above described amino, nitro, cyano, the above described alkyl, the above described alkenyl (other than styryl), the above described cycloalkyl, the above described alkoxy, the above described aromatic hydrocarbon, the above described aromatic heterocyclic, the above described aralkyl, the above described aryloxy, the above described alkoxy carbonyl or carboxyl (of which amino, alkyl, alkenyl, cycloalkyl, alkoxy, aromatic hydrocarbon, aromatic heterocyclic, aralkyl, aryloxy, and alkoxy carbonyl may be substituted).

The inventors of the present invention have found, after having extensively studied to solve the problems involved in the conventional organic EL material, that the organic layer can be stabilized by containing a compound shown by the general formula (A-I), (A-III), (A-VI) or (B-I), because they have excellent film-making properties and strongly amorphous to efficiently prevent agglomeration, with the result that the organic EL device of the present invention is highly durable.

Japanese Patent Laid-Open No. HEI 10-140146 discloses an organic EL device which uses the compound shown by the general formula (A-I) with hydrogen atom for each of the substituents $Z_1$ to $Z_4$ and $Z_7$ to $Z_{10}$, and hydrogen atom or methyl group for each of the substituents of $Z_5$ and $Z_6$. The inventors of the present invention have found, after having further developed the concept, that introduction of a substituent other than hydrogen atom into one or more of the substituents of $Z_1$ to $Z_4$ and $Z_7$ to $Z_{10}$ makes the molecular structure less planar, more distorted and more amorphous, to further stabilize the organic layer. It is also found that the similar effect is obtained to further stabilize the organic layer by introducing a bulky substituent in the ortho or meta position, like the compound shown by the general formula (A-III), rather than in the para position, and that the molecular structure is also distorted to stabilize the organic layer by introducing an alkyl group having 2 or more carbons, or aromatic hydrocarbon or aromatic heterocyclic group in the substituent $X_6$ or $X_7$, like the one shown by the general formula (A-VI), where the alkyl, aromatic hydrocarbon and aromatic heterocyclic groups may be substituted.

Moreover, it is possible to contain the compound shown by the general formula (A-I), (A-III), (A-VI) or (B-I) in the light-emitting region. The inventors of the present invention have found that the compounds shown by the general formula (A-I), (A-III), (A-VI) or (B-I) each have a very high fluorescence yield and thus the organic EL device emits EL light of higher brightness, when its light-emitting region contains one of the above compounds. The compound disclosed by Japanese Patent Laid-Open No. HEI 10-140146 exhibits light-emitting characteristics, but the inventors of the present invention have found, after having further developed the concept, that the compounds shown by the general formulae (A-I), (A-III), (A-VI) or (B-I) have better light-emitting characteristics.

Each of the compounds shown by the general formulae (A-I), (A-III), (A-VI) or (B-I) can form a light-emitting layer by itself, but can be doped with a light-emitting dopant to obtain the EL light emitted from the dopant. A known dopant can be used for the above purpose. It is also possible to use each of the compounds shown by the general formulae (A-I), (A-III), (A-VI) and (B-I) as the dopant. In this case, a known material can be used for the light-emitting host.

The layer containing the compound shown by the general formula (A-I), (A-III), (A-VI) or (B-I) preferably has a thickness of 1 to 1000 nm, more preferably 2 to 500 nm. An excessively thick film is undesirable, because it needs an excessively high driving voltage for the organic EL device. Because current flows into the organic EL device it will generate a large quantity of heat within the device, when its driving voltage is excessively high, to accelerate its aging.

The layer containing the compound shown by the general formula (A-I), (A-III), (A-VI) or (B-I) can be produced by a known method, e.g., vacuum deposition, more concretely, resistance heating, electron beam heating, sputtering, ion plating, MBE (molecular beam epitaxy), and so on.

It can be also produced by wet film-making methods, e.g., spin coating, spray coating, bar coating, dip coating, and roll coating.

A known solvent can be adequately used for preparing the coating solution. The solvents include, for example, alcohols, aromatic hydrocarbons, ketones, esters, aliphatic halogenated hydrocarbons, ethers, amides, sulfoxides or the like.

A polymer binder dispersed with at least the compound shown by the general formula (A-I), (A-III), (A-VI) or (B-I) may be used to prepare the layer containing the compound shown by the general formula (A-I), (A-III), (A-VI) or (B-I). The polymer binder can be selected from known substances, e.g., resins (e.g., vinyl-based resin, acrylic-based resin, epoxy-based resin, silicon-based resin, styryl-based resin, polyimide, polysilylene, polyvinyl carbazole, polycarbonate, cellulosic resin, polyolefin-based resin), and natural resins (e.g., glue and gelatin).

The polymer binder dispersed with the compound shown by the general formula (A-I), (A-III), (A-VI) or (B-I) may be formed into a film by a known method, e.g., the wet film-making method. A combination of the wet film-making method and solvent may be adequately selected from the known ones above described.

Tables I-1 to I-4 show examples of the compound shown by the general formula (A-I), which by no means limit the compound.

TABLE I-1

1

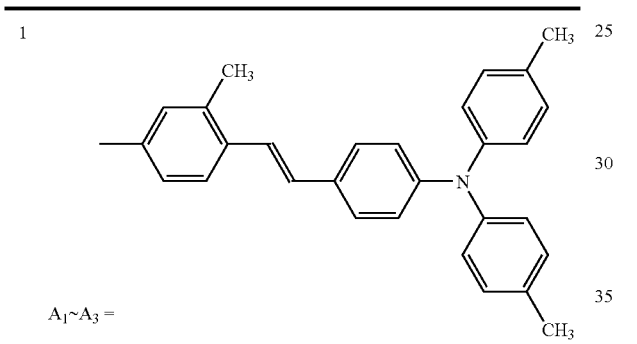

$A_1 \sim A_3 =$

2

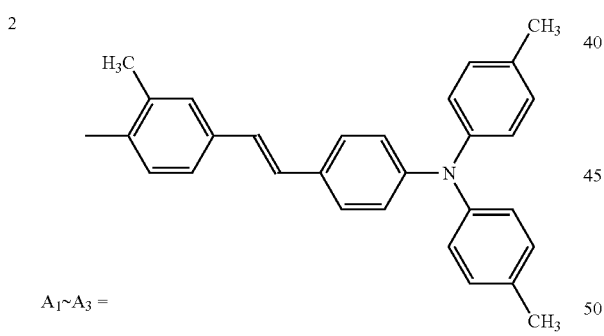

$A_1 \sim A_3 =$

3

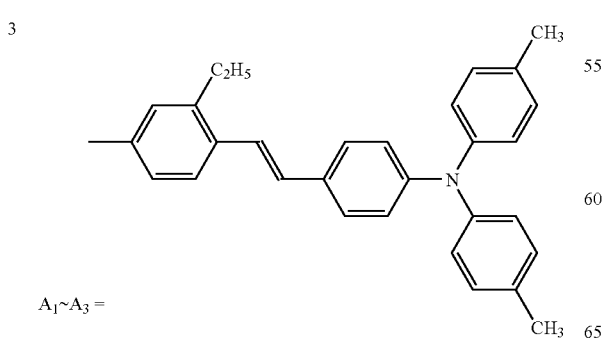

$A_1 \sim A_3 =$

TABLE I-1-continued

4

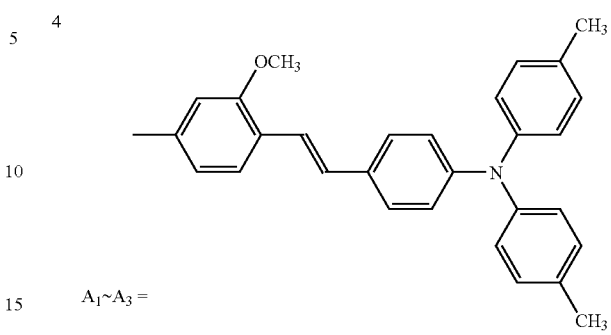

$A_1 \sim A_3 =$

5

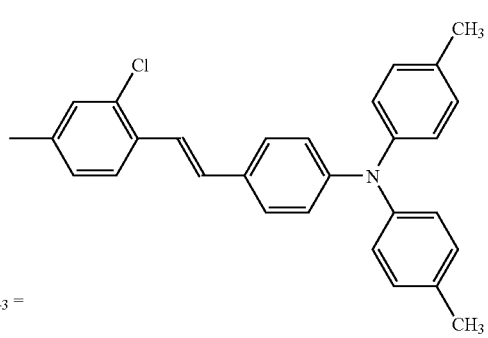

$A_1 \sim A_3 =$

6

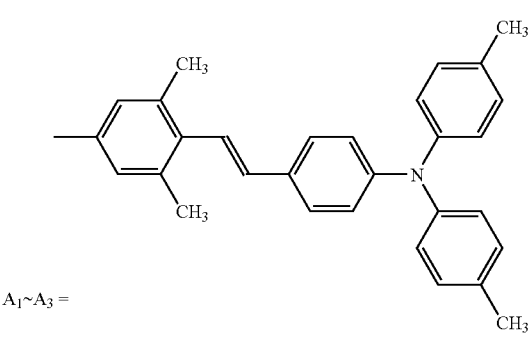

$A_1 \sim A_3 =$

TABLE I-2

7

$A_1 \sim A_3 =$ 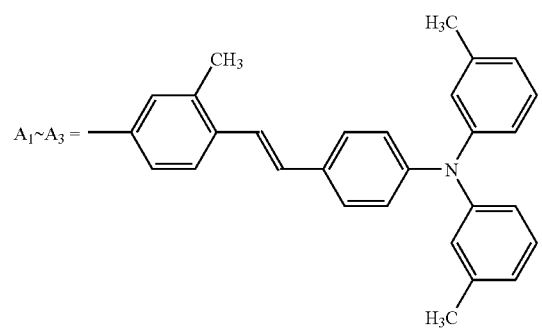

TABLE I-2-continued
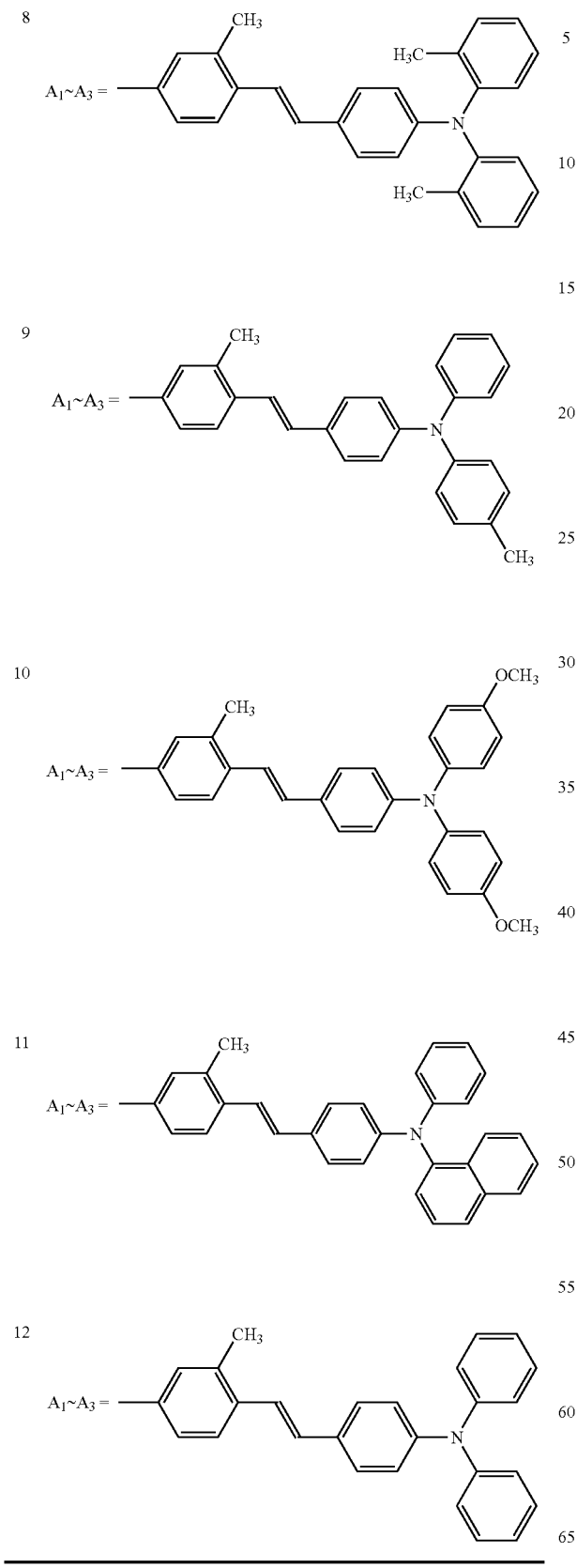
TABLE I-3
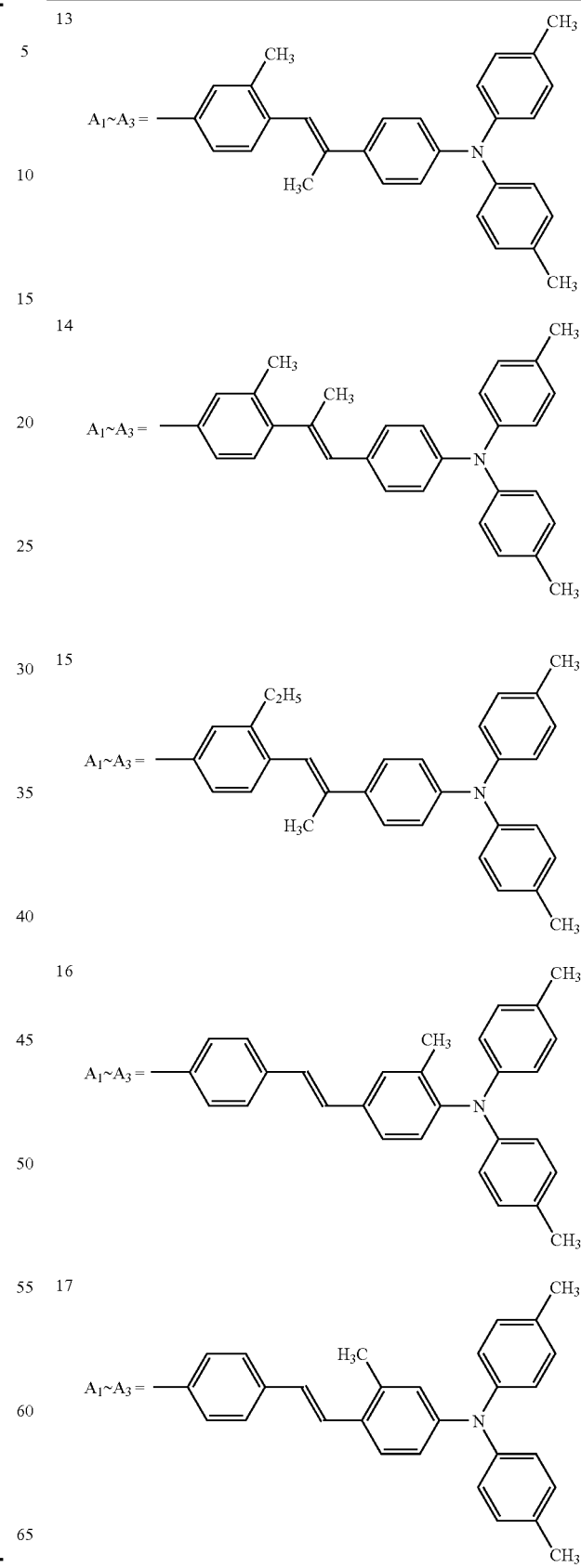

TABLE I-3-continued
18
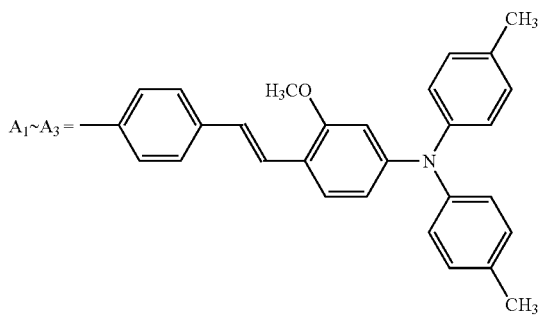
TABLE I-4
19
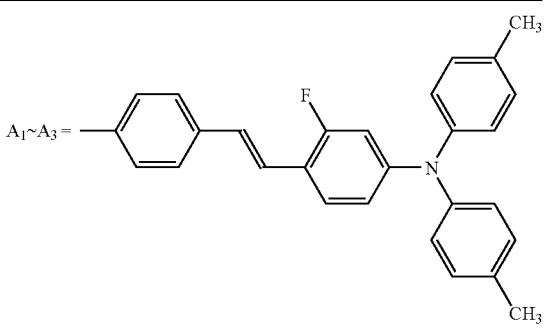
20
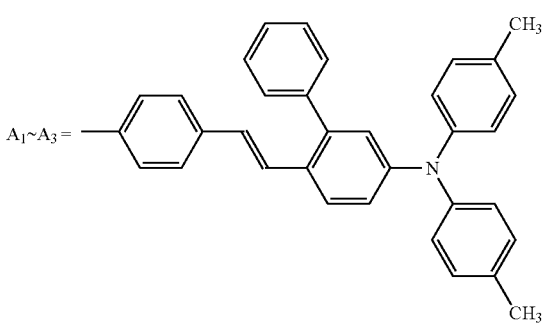
21
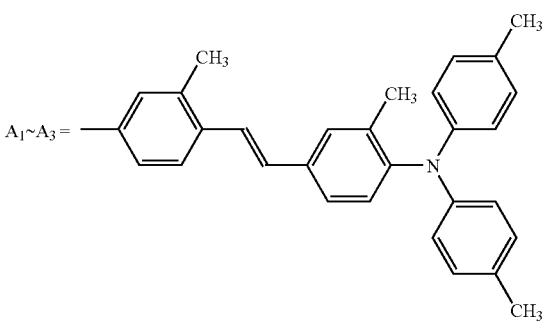
TABLE I-4-continued
22
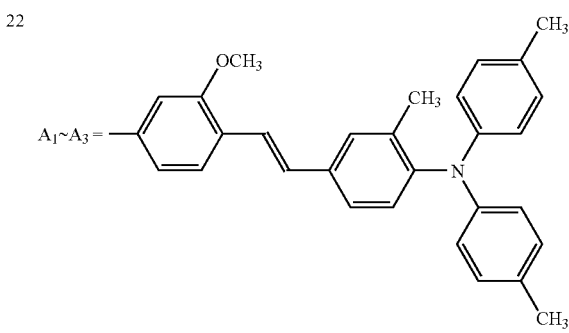
23
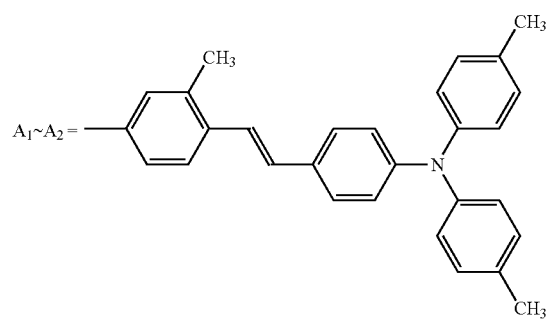
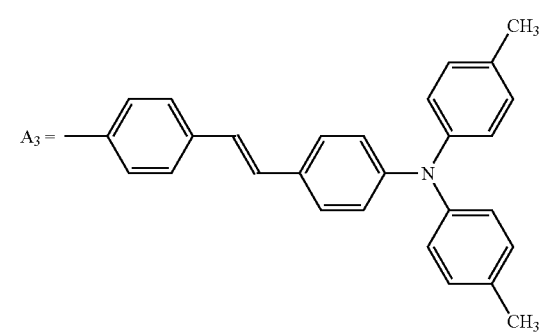
Table I-5 shows examples of the compound shown by the general formula (A-III), which by no means limit the compound.
TABLE I-5
24
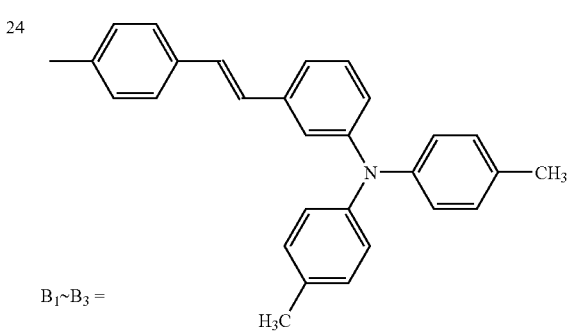

TABLE I-5-continued
25
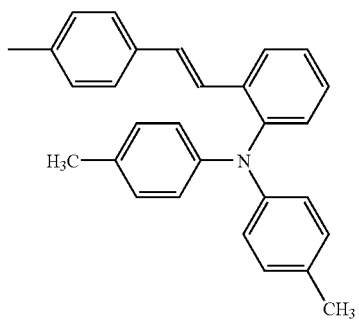
$B_1 \sim B_3 =$
26
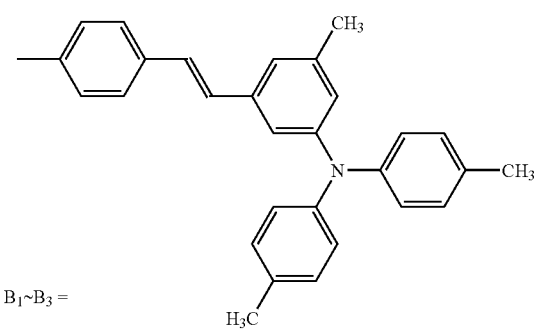
$B_1 \sim B_3 =$
27
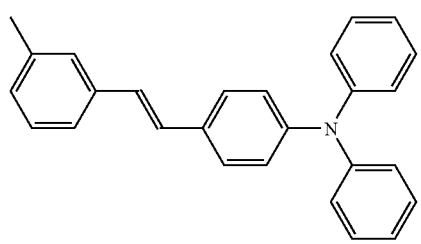
$B_1 \sim B_3 =$
Table I-6 shows examples of the compound shown by the general formula (A-VI), which by no means limit the compound.
TABLE I-6
28
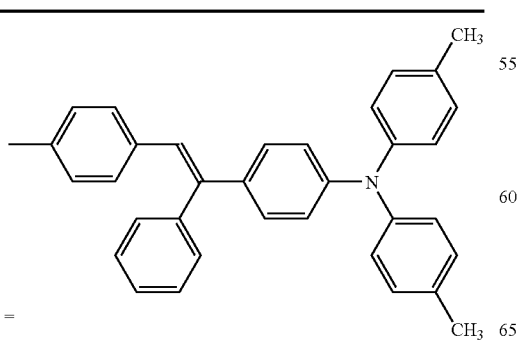
$D_1 \sim D_3 =$
TABLE I-6-continued
29
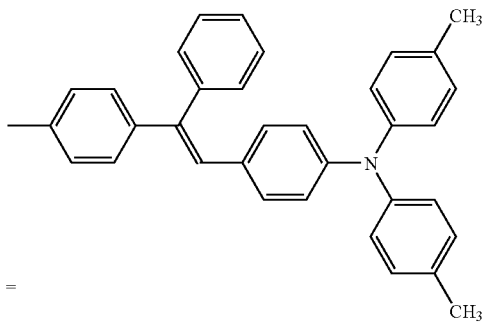
$D_1 \sim D_3 =$
30
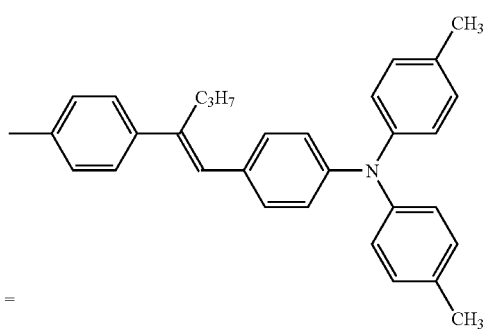
$D_1 \sim D_3 =$
Tables II-1 to II-6 show examples of the compound shown by the general formula (B-I), which by no means limit the compound.
TABLE II-1
1
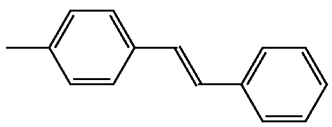
$a_1 =$
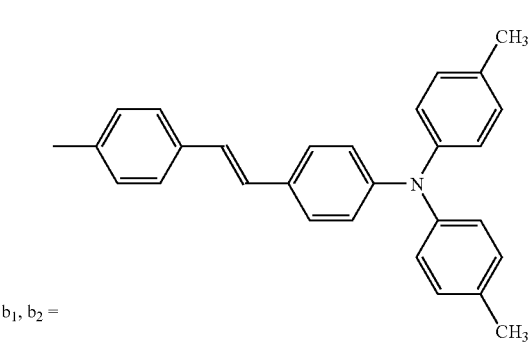
$b_1, b_2 =$ TABLE II-1-continued
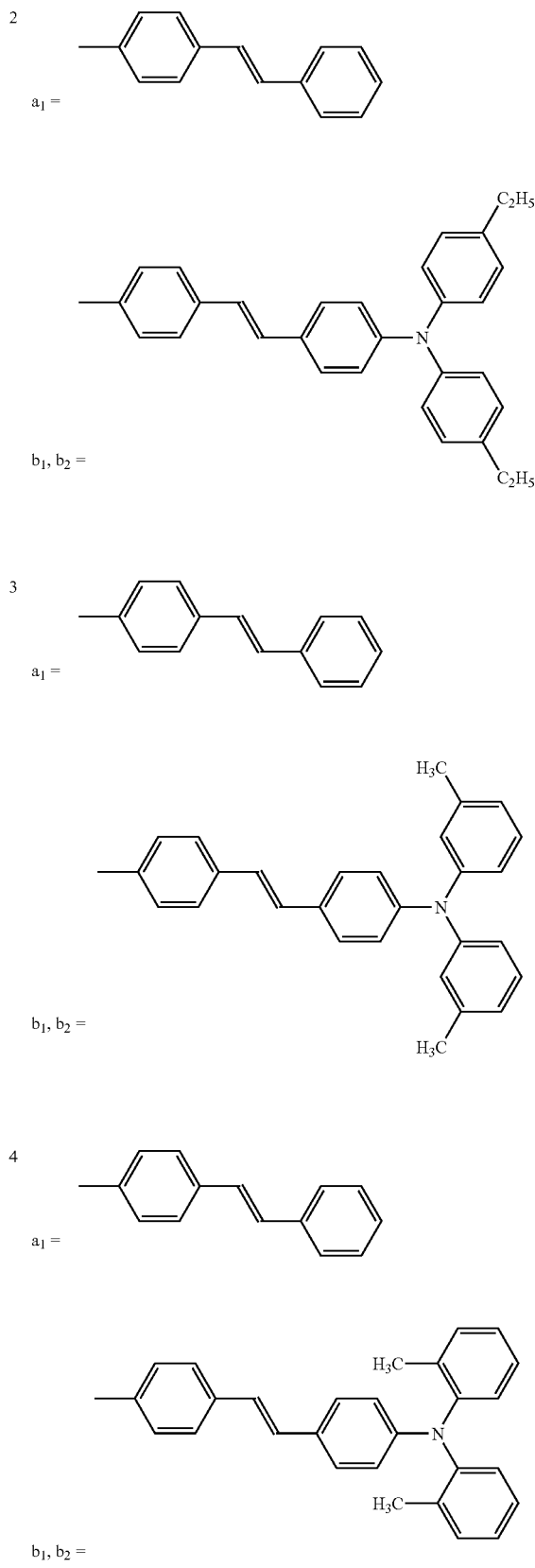
TABLE II-1-continued
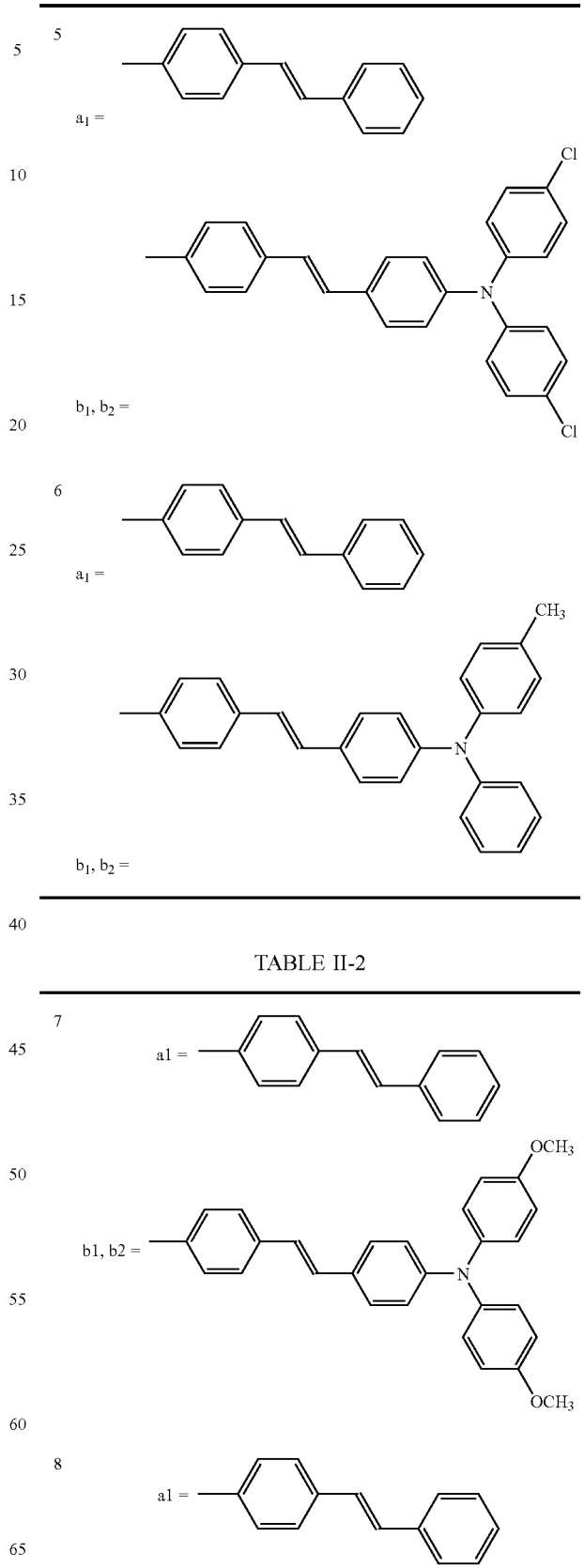
TABLE II-2

TABLE II-2-continued
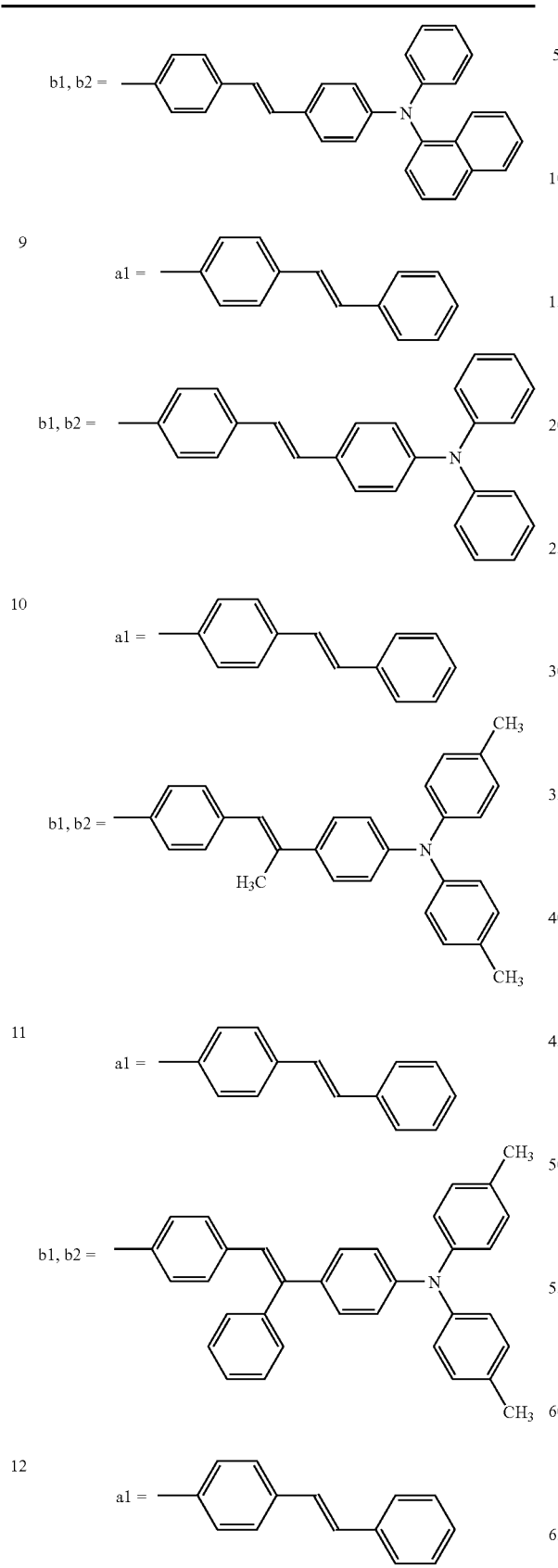
TABLE II-2-continued
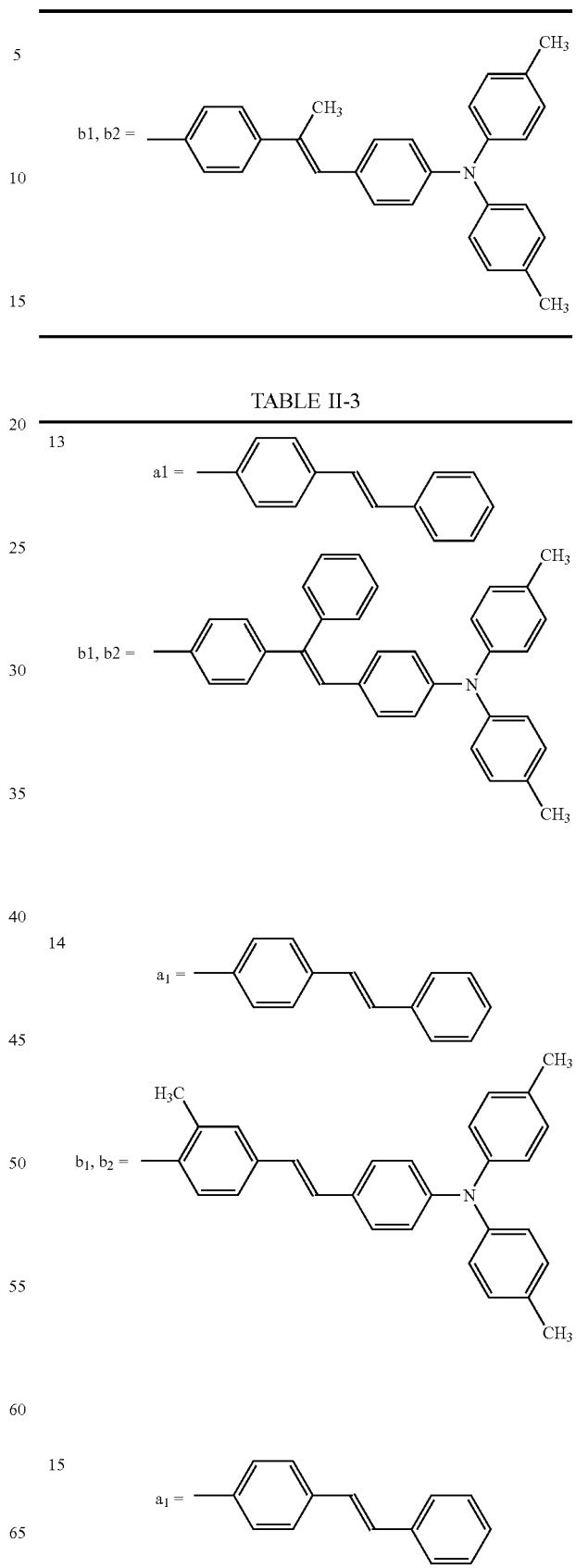
TABLE II-3

TABLE II-3-continued
| | |
|---|---|
| 5 | 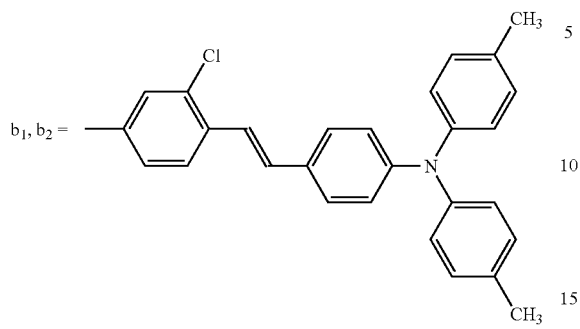 |
| 16 | 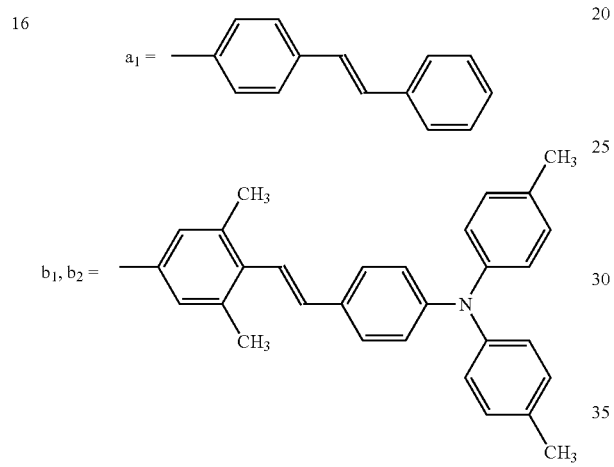 |
| 17 | 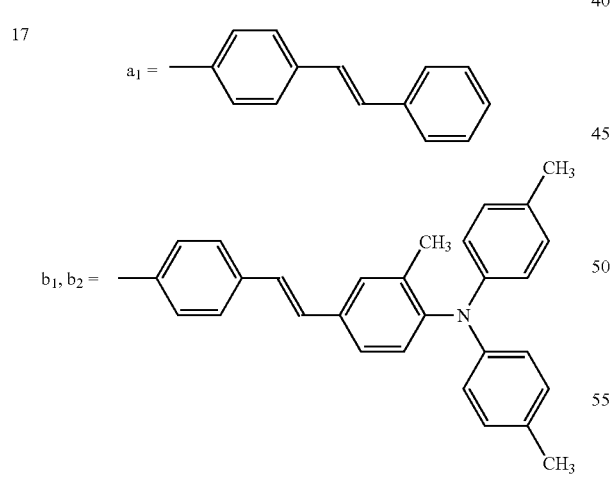 |
| 18 | 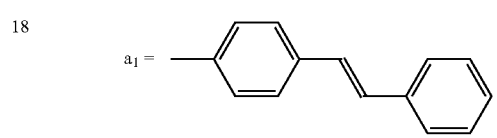 |
TABLE II-3-continued
| | |
|---|---|
| 6 | 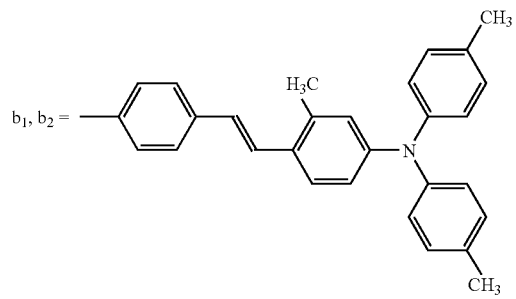 |
TABLE II-4
| | |
|---|---|
| 19 | 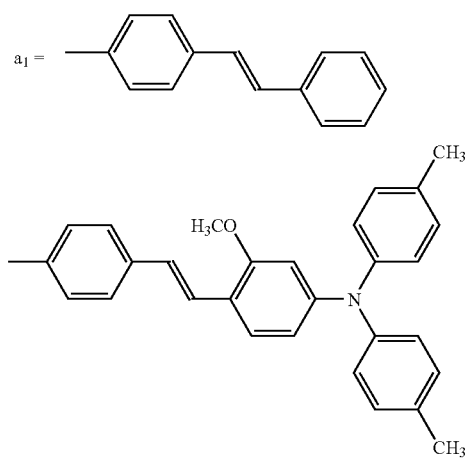 |
| 20 | 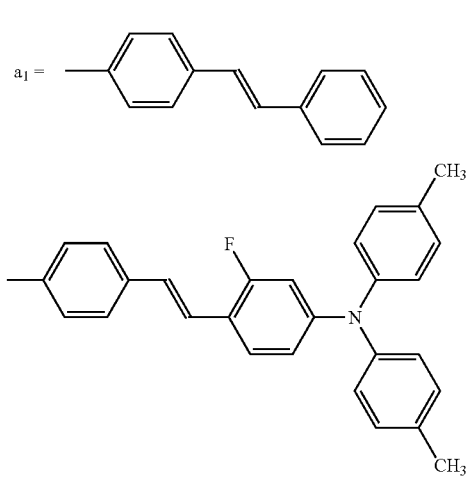 |
| 21 | 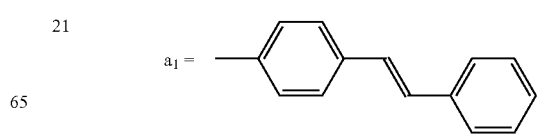 |

TABLE II-4-continued
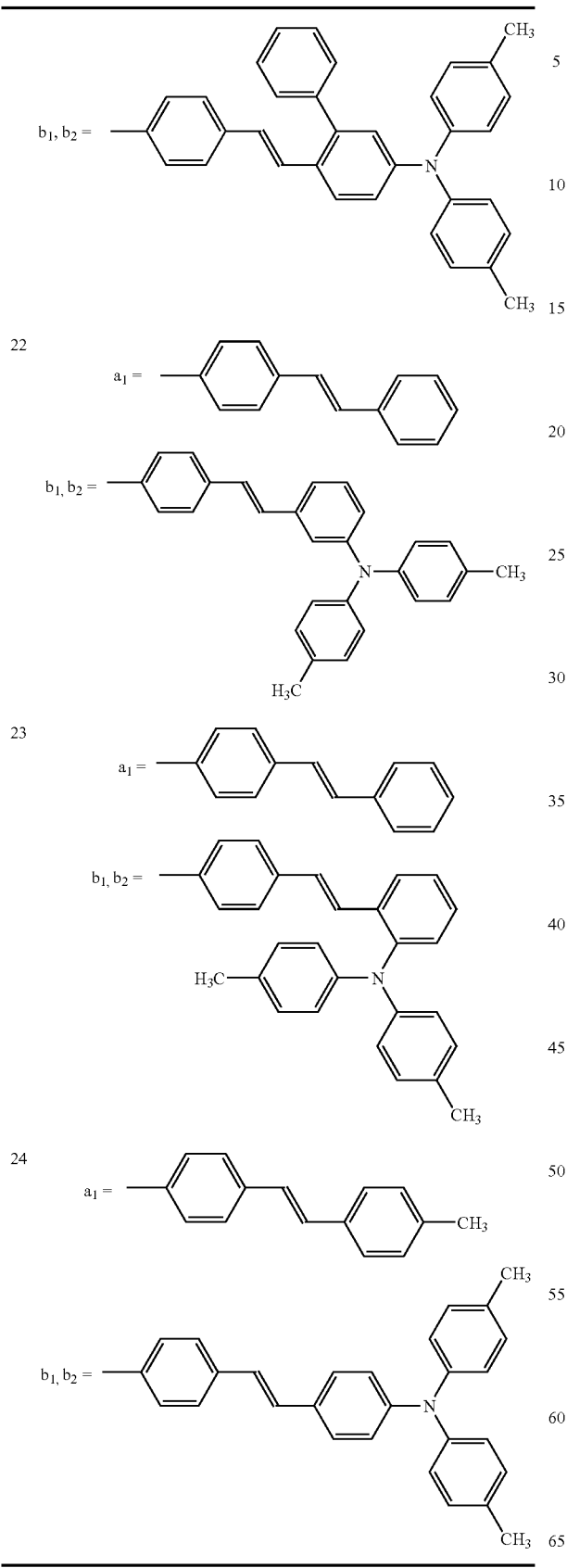
TABLE II-5
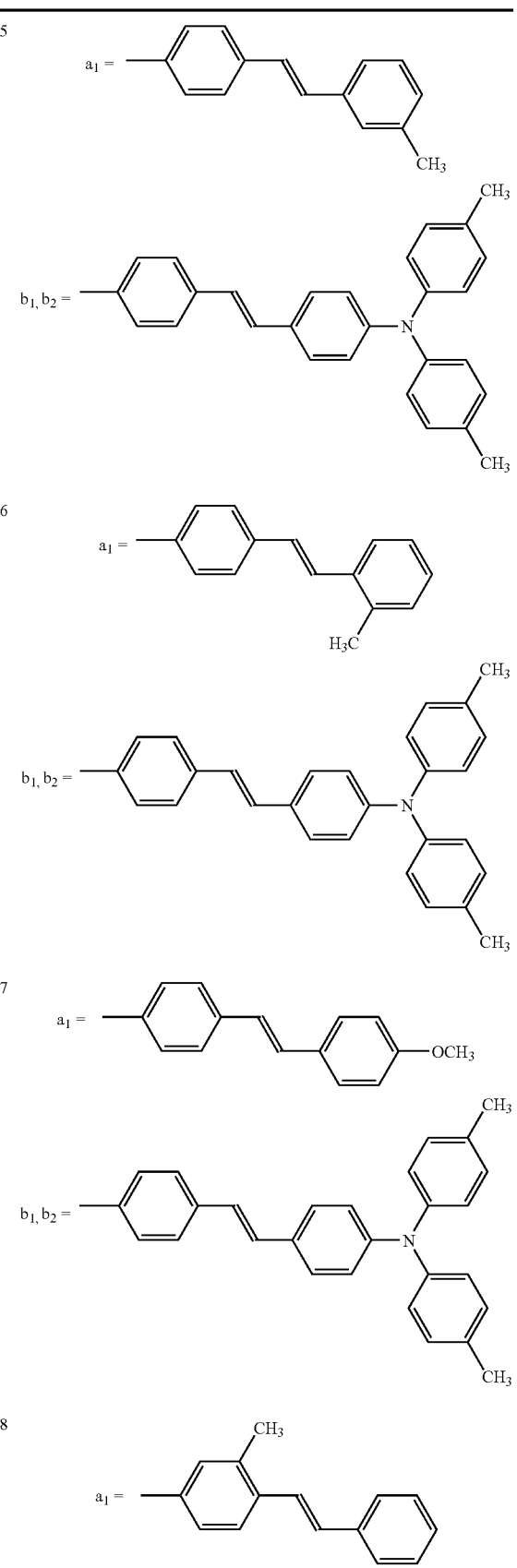

TABLE II-5-continued
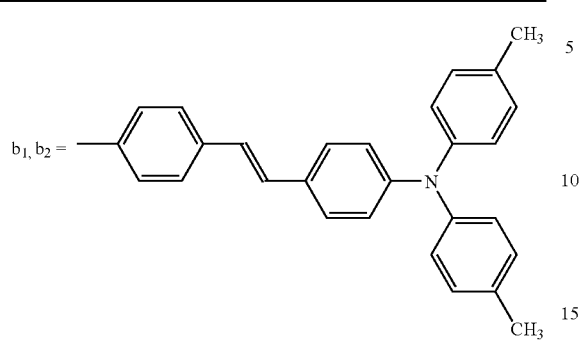
29
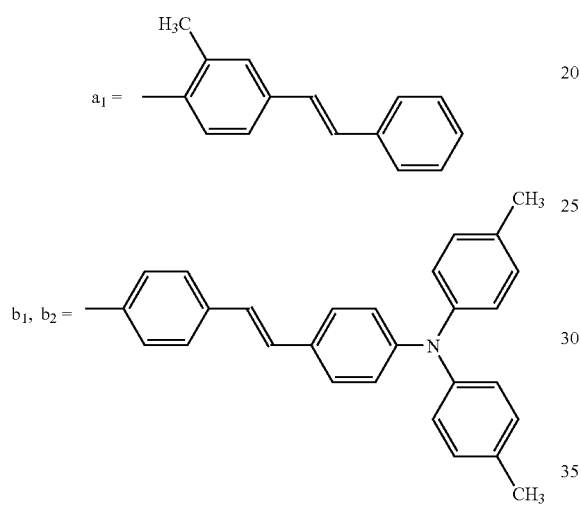
30
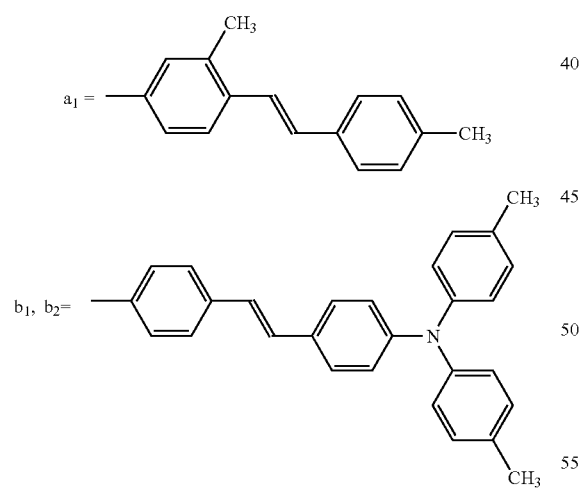
TABLE II-6
31
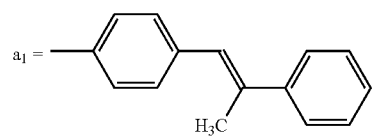
TABLE II-6-continued
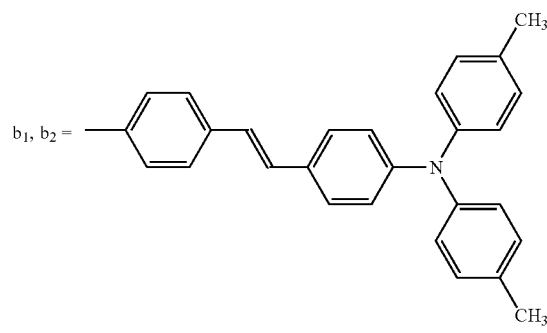
32
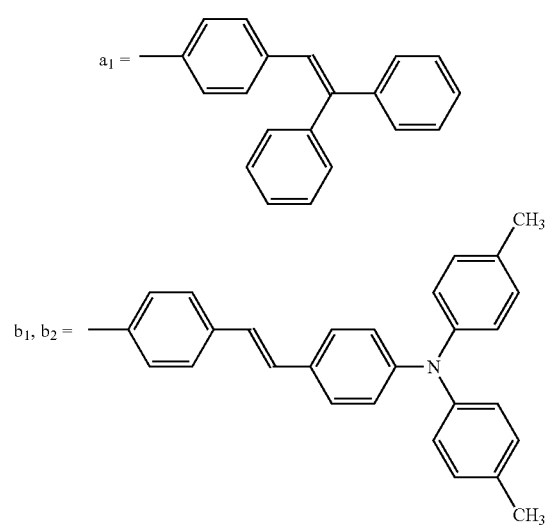
33
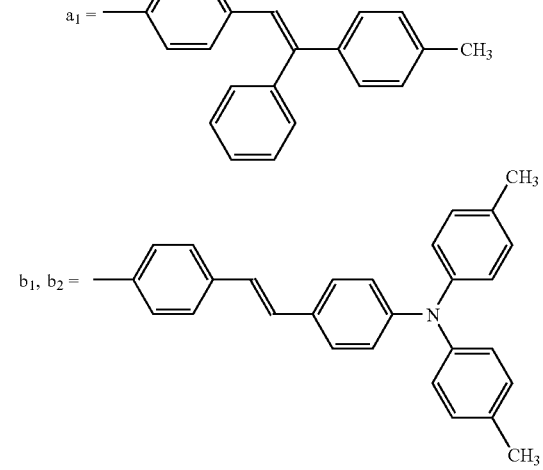
34
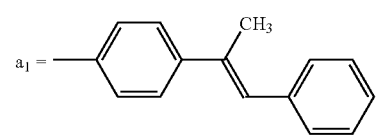

TABLE II-6-continued

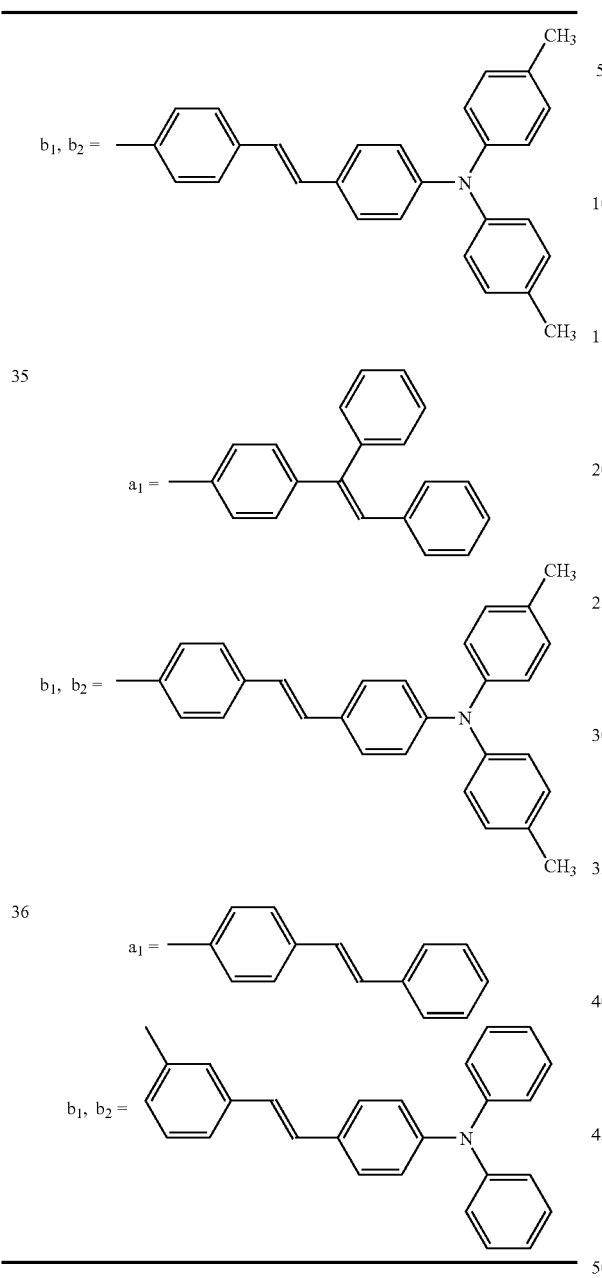

When the organic EL device of the present invention has the first hole transport layer of anode side containing the compound shown by the general formula (A-I), (A-III), (A-VI) or (B-I), and the second hole transport layer of light-emitting layer side containing an aromatic tertiary amine, the aromatic tertiary amine can be a known one. For example, those disclosed by Japanese Patent Publication No. HEI 6-32307, Japanese Patent Laid-Open No. HEI 5-234681, Japanese Patent Publication No. HEI 7-110940, and Japanese Patent Laid-Open Nos. HEI 5-239455 and HEI 6-312982 may be used for the present invention.

When the organic EL device of the present invention has an anode interface layer in contact with the anode, the anode interface layer may include a known compound. For example, a porphyrin-based compound disclosed by Japanese Patent Publication No. SHO 64-7635 may be used. The other compounds which can be used for the present invention include spiro, perylene, azo, quinone, indigo, polymethine, acridine or quinacridon compounds or the like.

A known organic fluorescent agent may be used for the EL light-emitting material. For example, those agents useful for the present invention include an anthracene-based compound, to begin with, metal complex of 8-quinolinol (Japanese Patent Laid-Open No. SHO 59-194393), and distyrylarylene derivative (Japanese Patent Laid-Open Nos. HEI 2-247278 and HEI 5-17765), which may be applicable as the light-emitting materials. The light-emitting host may be also doped with an organic fluorescent agent. The light-emitting dopants useful for the present invention include derivatives of cumarin, dicyanomethylenepiran, perylene (Japanese Patent Laid-Open No. SHO 63-264692), and quinacridon (Japanese Patent Laid-Open No. HEI 5-70773). They can be formed into a film by a known film-making method, e.g., vacuum deposition or coating.

Any layer for the present invention, except that containing the compound shown by the general formula (A-I), (A-III), (A-VI) or (B-I), may have any known composition. The electron transport region may be dispensed with. The materials for the anode and cathode may be selected from known ones.

EXAMPLES

The present invention is described more concretely by Examples.

Synthesis Example 1

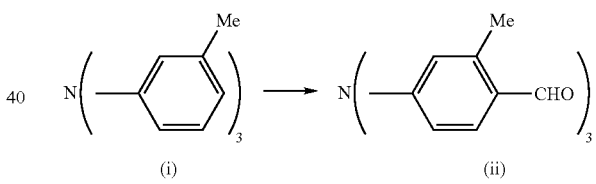

N,N-dimethylformamide and 3,3',3"-trimethyltriphenylamine (shown by the formula (i)) were put in an ice-cooled three-necked flask equipped with a drop funnel, a nitrogen gas leading pipe and a reflux condenser, and stirred in a nitrogen atmosphere, to which phosphorus oxychloride was slowly added dropwise by the drop funnel. On completion of the addition, the temperature of the mixture was raised up to 80° C. slowly and kept 80° C. for 10 hours with stirring. After on completion of the reactions water was added thereto, the mixture was stirred for 15 min. The mixture was purified by the common method, to obtain 3,3',3"-trimethyl-4,4',4"-triformyltriphenylamine (shown by the formula (ii)).

[Formula 16]

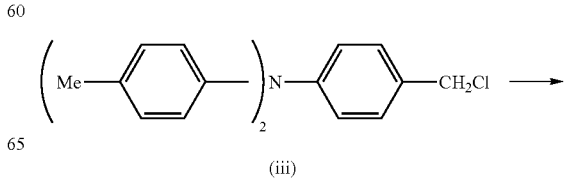

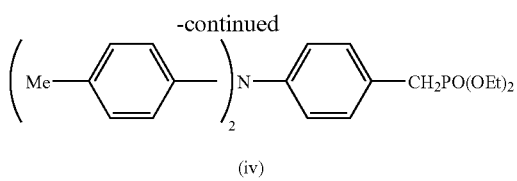

(iv)

4-chloromethyl-4',4"-dimethyltriphenylamine (shown by the formula (iii)) and triethyl phosphate were put in a three-necked flask equipped with a reflux condenser, to which toluene was added and heated with stirring for 8 hours under reflux. The mixture was purified by the common method, to obtain 4-(4',4"-dimethyldiphenylamino)benzyl diethyl phosphonate (shown by the formula (iv)).

[Formula 17]

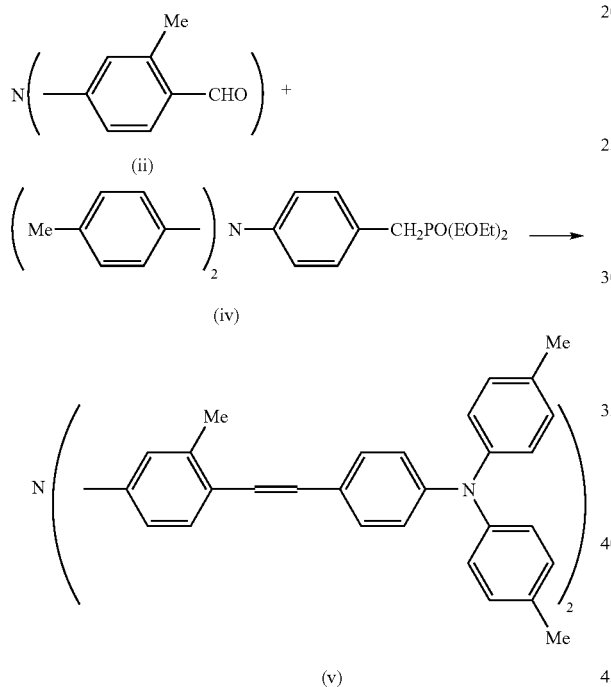

3,3',3"-trimethyl-4,4',4"-triformyltriphenylamine (shown by the formula (ii)) was reacted with 4-(4',4"-dimethyldiphenylamino)benzyl diethyl phosphonate (shown by the formula (iv)) in a solution of N,N-dimethylformamide suspended with hydrogenated sodium at 40° C. for 40 hours. The mixture was purified by common method, to obtain 3,3',3"-trimethyl-4,4',4"-tris(4-(N,N-ditolylamino)styryl)triphenylamine (shown by the formula (v)).

Synthesis Example 2

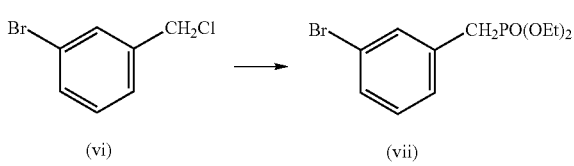

3-bromobenzyl chloride shown by the formula (vi) and triethyl phosphite were put in a three-necked flask equipped with a reflux condenser, to which toluene was added and heated with stirring for 8 hours under reflux. The mixture was purified by common method, to obtain diethyl 3-bromobenzylphosphonate shown by the formula (vii).

Diethyl 3-bromobenzylphosphonate shown by the formula (vii) was reacted with 4-formyltriphenylamine shown by the formula (viii) in a solution of N,N-dimethylformamide suspended with hydrogenated sodium at 40° C. for 40 hours. The mixture was purified by the common method, to obtain 4-(3-bromostyryl)triphenylamine shown by the formula (ix).

[Formula 20]

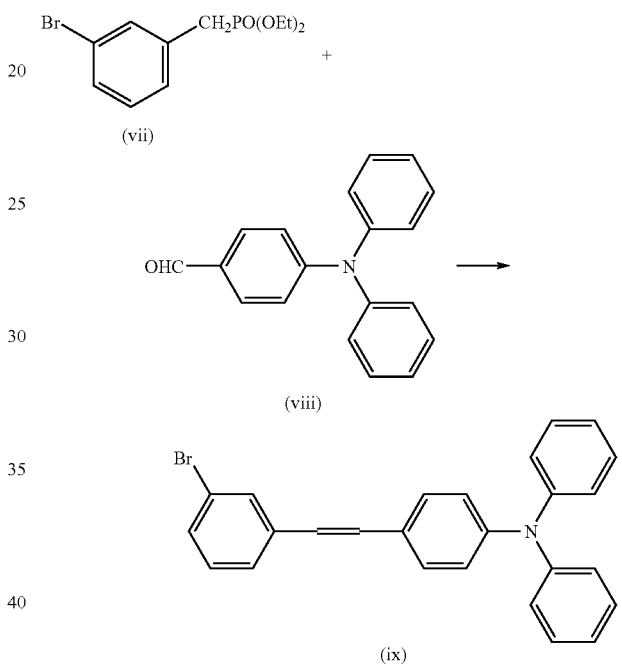

4-(3-bromostyryl)triphenylamine (shown by the formula (ix)) and tetrahydrofuran were put in a three-necked flask equipped with a drop funnel and dryer tube, and stirred. The mixture was cooled to −78° C., to which a hexane solution of butyl lithium was added dropwise by a drop funnel. The temperature of the mixture was kept at −78° C. for 1 hour and then raised upto −20° C. with stirring. A toluene solution of nitrogen chloride was slowly added dropwise by a drop funnel. On completion of the addition, it was further stirred for two hours. The mixture was purified by common method, to obtain 3,3',3"-tris-(4-diphenylaminostyryl)triphenylamine (shown by the formula (x)).

Example 1

Figure 2A:
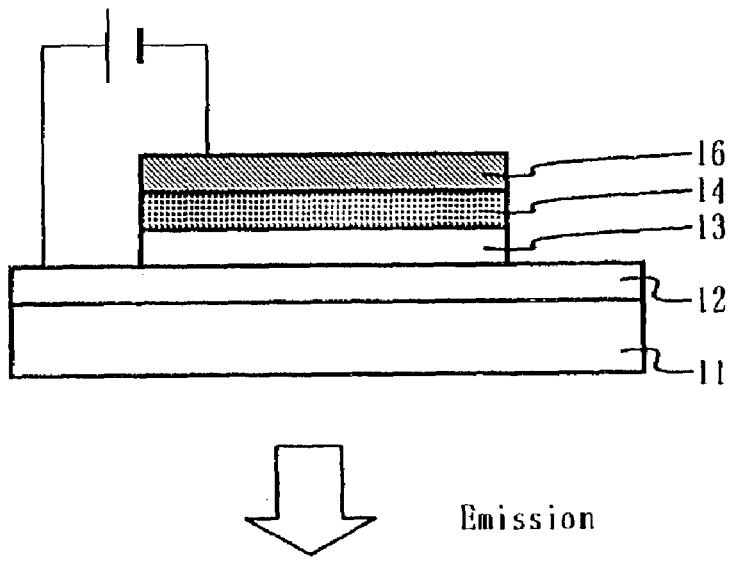
FIG. 2A and FIG. 2B show another example of the sectional view of the organic EL device of the present invention.
Figure 2B:
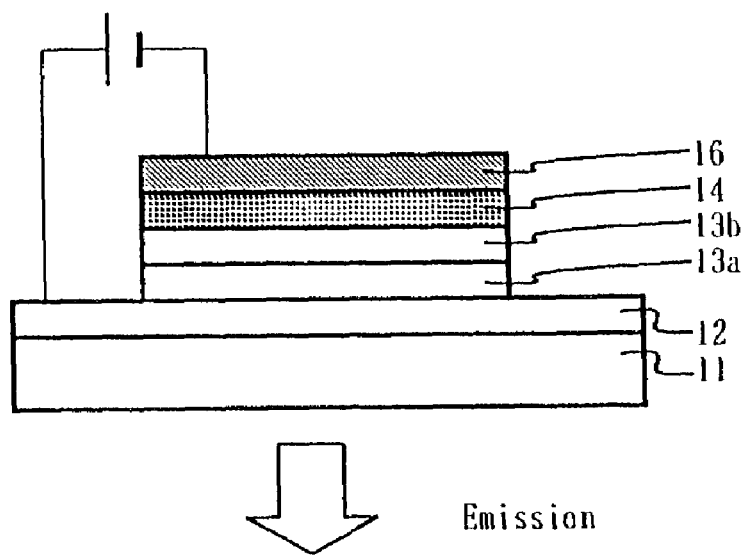
Figure 3:
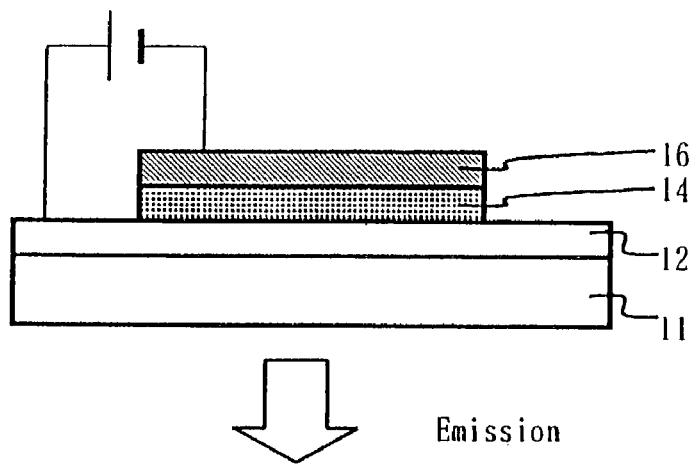
FIG. 3 shows still another example of the sectional view of the organic EL device of the present invention.

Referring to FIG. 2(a), a glass substrate 11 was coated with a thin film of ITO (indium tin oxide) as the anode 12, having a resistivity of 20 Ω/□, by sputtering, the compound 1 shown by Table I-1 to a thickness of 50 nm as the hole transport layer 13 by resistance heating vacuum deposition, tris-(8-hydroxyquinolinol) aluminum (compound (a)) to a thickness of 60 nm as the light-emitting layer 14 also by resistance heating vacuum deposition, and finally MgAg (deposition rate ratio; 10:1) to a thickness of 150 nm as the cathode 16 also by resistance heating vacuum deposition, in this order.

Compound (a)

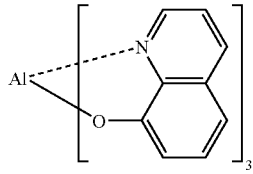

Very bright green color planar-emission was performed from the light-emitting layer of tris-(8-hydroxyquinolinol) aluminum. Brightness of the light was 203 cd/m² initially at a constant current density of 10 mA/cm² in a dried nitrogen atmosphere, and 147 cd/m² after 1000 hours drive, by which is meant that this organic EL device of the present invention is more durable than those prepared by Comparative Examples 1 and 2.

Examples 2 to 6

The same procedure as used for Example 1 was repeated, except that the material applied to the hole transport layer was replaced by the compound shown by Table I-7, to prepare the organic EL devices. They emitted very bright green color emission from the light-emitting layers of tris-(8-hydroxyquinolinol) aluminum. Brightness of the emitted light initial and after 1000 hours drive, is given in Table I-7 for each device, at a constant current density of 10 mA/cm² in a dried nitrogen atmosphere.

TABLE I-7

| Examples | Hole transport layer | Initial brightness (cd/m²) | Brightness after 1000 hours drive (cd/m²) |
|---|---|---|---|
| 2 | Compound 10 shown by Table I-2 | 231 | 150 |
| 3 | Compound 16 shown by Table I-3 | 216 | 179 |
| 4 | Compound 24 shown by Table I-5 | 205 | 151 |
| 5 | Compound 27 shown by Table I-5 | 210 | 161 |
| 6 | Compound 28 shown by Table I-6 | 237 | 177 |

Example 7

Referring to FIG. 2(b), a glass substrate 11 was coated with a thin film of ITO as the anode 12, having a resistivity of 20 Ω/□, by sputtering, the compound 1 shown by Table I-1 to a thickness of 40 nm as the first hole transport layer 13a by resistance heating vacuum deposition, compound (b) to a thickness of 20 nm as the second hole transport layer 13b also by resistance heating vacuum deposition, tris-(8-hydroxyquinolinol) aluminum (compound (a)) to a thickness of 50 nm as the light-emitting layer 14 also by resistance heating vacuum deposition, and finally MgAg (deposition rate ratio; 10:1) to a thickness of 150 nm as the cathode 16 also by resistance heating vacuum deposition.

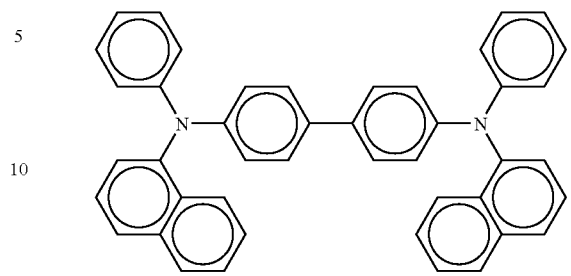

Compound (b)

Very bright green color planar-emission was performed from the light-emitting layer of tris-(8-hydroxyquinolinol) aluminum. Brightness of the light was 273 cd/m² initially at a constant current density of 10 mA/cm² in a dried nitrogen atmosphere, and 225 cd/m² after 1000 hours drive.

Examples 8 to 12

The same procedure as used for Example 7 was repeated, except that the material applied to the first hole transport layer was replaced by the compound shown by Table I-8, to prepare the organic EL devices. They emitted very bright green color emission from the light-emitting layers of tris-(8-hydroxyquinolinol) aluminum. Brightness of the emitted light, initial and after 1000 hours drive, is given in Table I-8 for each device, at a constant current density of 10 mA/cm² in a dried nitrogen atmosphere.

TABLE I-8

| Examples | First hole transport layer | Initial brightness (cd/m²) | Brightness after 1000 hours drive (cd/m²) |
|---|---|---|---|
| 8 | Compound 10 shown by Table I-2 | 291 | 232 |
| 9 | Compound 16 shown by Table I-3 | 253 | 199 |
| 10 | Compound 24 shown by Table I-5 | 256 | 194 |
| 11 | Compound 27 shown by Table I-5 | 280 | 241 |
| 12 | Compound 28 shown by Table I-6 | 266 | 217 |

Example 13

Referring to FIG. 2(a), a glass substrate 11 was coated with a thin film of ITO as the anode 12, having a resistivity of 20 Ω/□, by sputtering. The anode 12 was coated with a solution, which was a mixture of the compound 1 of Table I-1 and polycarbonate (Mitsubishi Chemical, Z200) (1:1 by weight) dissolved in tetrahydrofuran at 1.5 wt. %, by dip coating to a thickness of 50 nm, and dried at 80° C. for 1 hour, to form the hole transport layer 13. It was then coated with tris-(8-hydroxyquinolinol) aluminum (compound (a)) to a thickness of 50 nm as the light-emitting layer 14 by resistance heating vacuum deposition, and finally MgAg (deposition rate ratio; 10:1) to a thickness of 150 nm as the cathode 16 also by resistance heating vacuum deposition.

Very bright green color planar-emission was performed from the light-emitting layer of tris-(8-hydroxyquinolinol) aluminum. Brightness of the light was 212 cd/m² initially at a constant current density of 10 mA/cm² in a dried nitrogen atmosphere, and 180 cd/m² after 1000 hours drive.

Example 14

Referring to FIG. 2(a), a glass substrate 11 was coated with a thin film of ITO as the anode 12, having a resistivity of 20 Ω/□, by sputtering. The anode 12 was coated with the compound 1 of Table I-1 and compound (b) by resistance heating vacuum deposition to a thickness of 50 nm (codeposition at a rate ratio of 7:3), to form the hole transport layer 13. It was then coated with tris-(8-hydroxyquinolinol) aluminum (compound (a)) to a thickness of 50 nm as the light-emitting layer 14 also by resistance heating vacuum deposition, and finally MgAg (deposition rate ratio; 10:1) to a thickness of 150 nm as the cathode 16 also by resistance heating vacuum deposition.

Very bright green color planar-emission was performed from the light-emitting layer of tris-(8-hydroxyquinolinol) aluminum. Brightness of the light was 276 cd/m² initially at a constant current density of 10 mA/cm² in a dried nitrogen atmosphere, and 212 cd/M² after 1000 hours drive.

Example 15

Referring to FIG. 1(a), a glass substrate 11 was coated with a thin film of ITO (indium tin oxide) as the anode 12, having a resistivity of 20 Ω/□, by sputtering, the compound 1 of Table I-1 to a thickness of 50 nm as the hole transport layer 13 by resistance heating vacuum deposition, tris-(8-hydroxyquinolinol) aluminum (compound (a)) and DCM (compound (c)) to a thickness of 30 nm as the light-emitting layer 14 also by resistance heating vacuum deposition (codeposition at a rate ratio of 100:2), tris-(8-hydroxyquinolinol) aluminum to a thickness of 30 nm as the electron transport layer 15 also by resistance heating vacuum deposition, and finally MgAg (deposition rate ratio: 10:1) to a thickness of 150 nm as the cathode 16 also by resistance heating vacuum deposition, in this order.

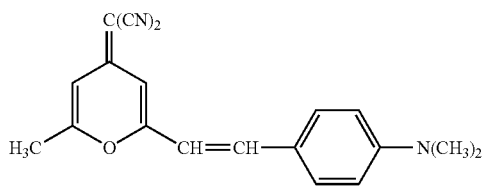

Compound (c)

Very bright orange color planar-emission was performed from the light-emitting layer of DCM. Brightness of the light was 479 cd/m² initially at a constant current density of 10 mA/cm² in a dried nitrogen atmosphere, and 387 cd/m² after 1000 hours drive.

Example 16

Referring to FIG. 4, a glass substrate 11 was coated with a thin film of ITO (indium tin oxide) as the anode 12, having a resistivity of 20 Ω/□, by sputtering, copper phthalocyanine (compound (d)) to a thickness of 10 nm as the anode interface layer 17 by resistance heating vacuum deposition, the compound 1 of Table I-1 to a thickness of 50 nm as the hole transport layer 13 also by resistance heating vacuum deposition, tris-(8-hydroxyquinolinol) aluminum (compound (a)) to a thickness of 50 nm as the light-emitting layer 14 also by resistance heating vacuum deposition, and finally MgAg (deposition rate ratio: 10:1) to a thickness of 150 nm as the cathode 16 also by resistance heating vacuum deposition, in this order.

Very bright green color planar-emission was performed from the light-emitting layer of tris-(8-hydroxyquinolinol) aluminum. Brightness of the light was 223 cd/m² initially at a constant current density of 10 mA/cm² in a dried nitrogen atmosphere, and 185 cd/m² after 1000 hours drive.

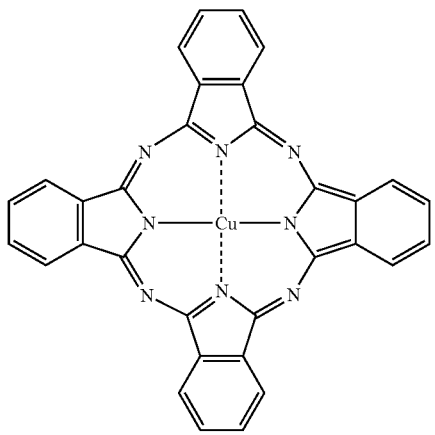

Compound (d)

Example 17

Referring to FIG. 1(a), a glass substrate 11 was coated with a thin film of ITO (indium tin oxide) as the anode 12, having a resistivity of 20 Ω/□, by sputtering, the compound (b) to a thickness of 50 nm as the hole transport layer 13 by resistance heating vacuum deposition, compound 1 of Table I-1 to a thickness of 50 nm as the light-emitting layer 14 also by resistance heating vacuum deposition, t-Bu-PBD (compound (e)) to a thickness of 30 nm as the electron transport layer 15 also by resistance heating vacuum deposition, and finally MgAg (deposition rate ratio: 10:1) to a thickness of 150 nm as the cathode 16 also by resistance heating vacuum deposition, in this order.

Very bright blue color planar-emission was performed from the light-emitting layer of the compound 1 of TableI-1. Brightness of the light was 711 cd/m² at a voltage of 8 V, by which is meant that this device has improved brightness characteristics over the one prepared by Comparative Example 3.

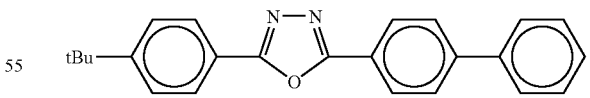

Compound (e)

Examples 18 to 22

The same procedure as used for Example 17 was repeated, except that the material applied to the light-emitting layer was replaced by the compound shown by Table I-9, to prepare the organic EL devices. They emitted very bright emission from the light-emitting layers. Brightness of the emitted light at a voltage of 8 V is given in Table I-9 for each device.

TABLE I-9

| Examples | Light-emitting layer | Brightness at 8 V (cd/m$^2$) |
| --- | --- | --- |
| 18 | Compound 10 shown by Table I-2 | 808 |
| 19 | Compound 16 shown by Table I-3 | 537 |
| 20 | Compound 24 shown by Table I-5 | 726 |
| 21 | Compound 27 shown by Table I-5 | 652 |
| 22 | Compound 28 of Table I-6 | 616 |

Example 23

Referring to FIG. 1(a), a glass substrate 11 was coated with a thin film of ITO as the anode 12, having a resistivity of 20 Ω/□, by sputtering, and the compound (b) to a thickness of 50 nm as the hole transport layer 13 by resistance heating vacuum deposition, in this order. The hole transport layer 13 was coated with the compound 1 of Table I-1 and rubrene (compound (f) to a thickness of 50 nm also by resistance heating vacuum deposition (codeposition at a rate ratio of 100:2), to form the light-emitting layer 14. It was then coated with t-Bu-PBD (compound (e)) to a thickness of 30 nm as the electron transport layer 15 also by resistance heating vacuum deposition, and finally MgAg (deposition rate ratio: 10:1) to a thickness of 150 nm as the cathode 16 also by resistance heating vacuum deposition, in this order.

It emitted very bright yellow color emission from the light-emitting layer of the compound (f). Brightness of the light was 1835 cd/m$^2$ at a voltage of 8 V.

Compound (f)

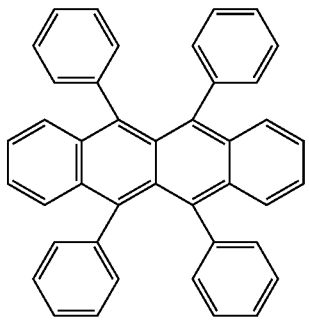

Synthesis Example 3

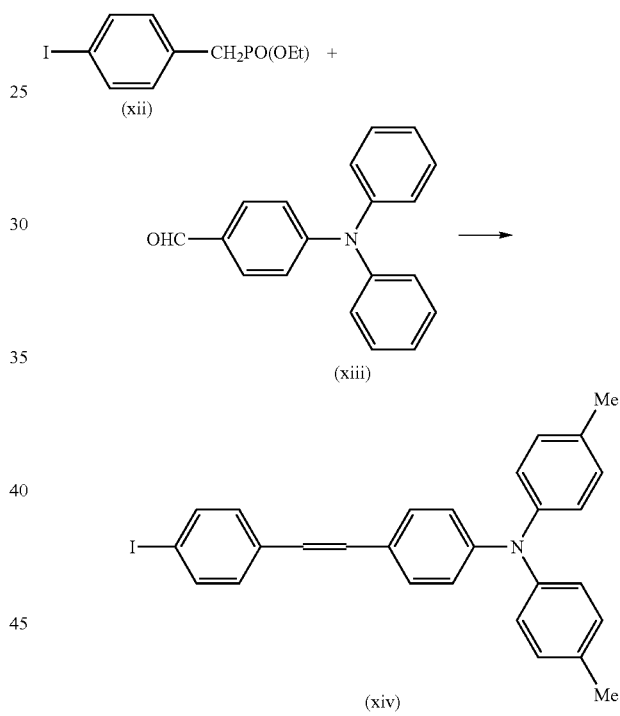

4-iodobenzyl chloride and triethyl phosphite were put in a three-necked flask equipped with a reflux condenser, to which toluene was added and heated with stirring for 8 hours under reflux. The mixture was purified by the common method, to obtain diethyl 4-iodobenzylphosphonate.

Diethyl 4-iodobenzylphosphonate (shown by the formula (xii)) was reacted with 4-formyl-4',4"-dimethyltriphenylamine (shown by the formula (viii)) in a solution of N,N-dimethylformamide suspended with hydrogenated sodium at 40° C. for 40 hours. The mixture was purified by the common method, to obtain 4-(4-iodostyryl)-4',4"-dimethyltriphenylamine (shown by the formula (xiv)).

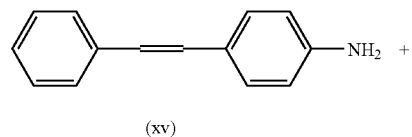

(xv)

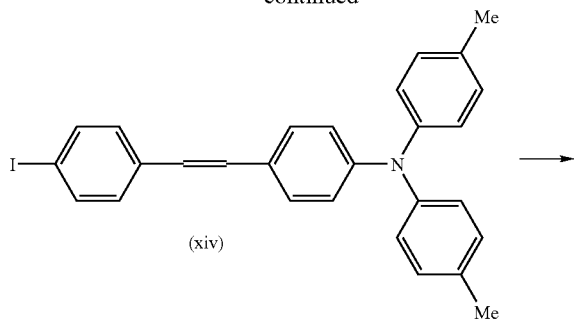

(xiv)

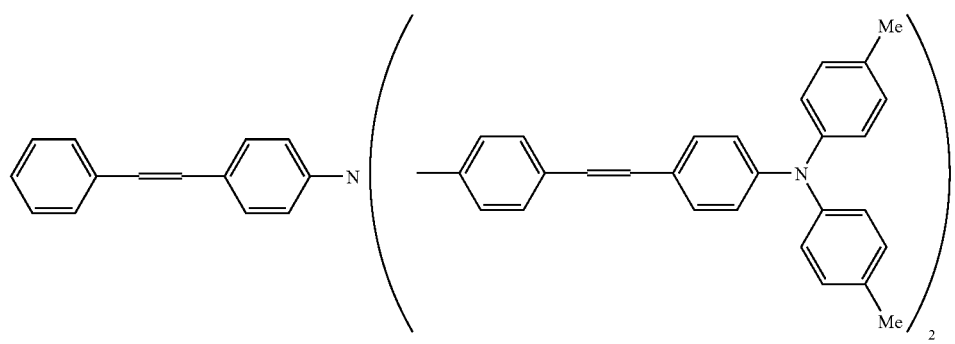

(xvi)

4-styrylaniline (shown by the formula (xv)), 4-(4-iodostyryl)-4',4"-dimethyltriphenylamine (shown by the formula (xiv)), copper powder and potassium carbonate were added to nitrobenzene, and they were allowed to react with one another at 200° C. for 40 hours. The mixture was purified by the common method, to obtain 4-styryl-4',4"-bis(4-(N,N-ditolylamino)styryl)triphenylamine (shown by the formula (xvi)).

Synthesis Example 4

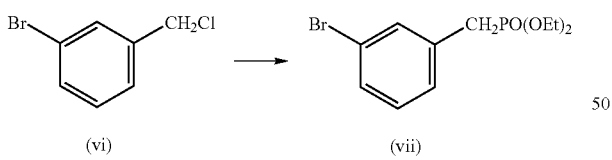

(vi)　　　　　　　　(vii)

3-bromobenzyl chloride (shown by the formula (vi)) and triethyl phosphite were put in a three-necked flask equipped with a reflux condenser, to which toluene was added and heated with stirring for 8 hours under reflux. The mixture was purified by the common method, to obtain diethyl 3-bromobenzylphosphonate (shown by the formula (vii)).

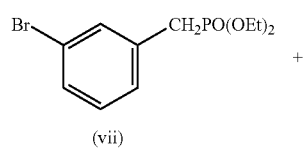

(vii)

+

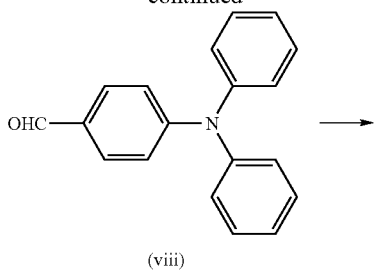

(viii)

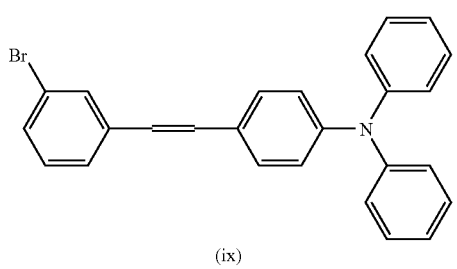

(ix)

Diethyl 3-bromobenzylphosphonate (shown by the formula (vii)) was reacted with 4-formyltriphenylamine (shown by the formula (viii)) in a solution of N,N-dimethylformamide suspended with hydrogenated sodium at 40° C. for 40 hours. The mixture was purified by common method, to obtain 4-(3-bromostyryl)triphenylamine (shown by the formula (ix)).

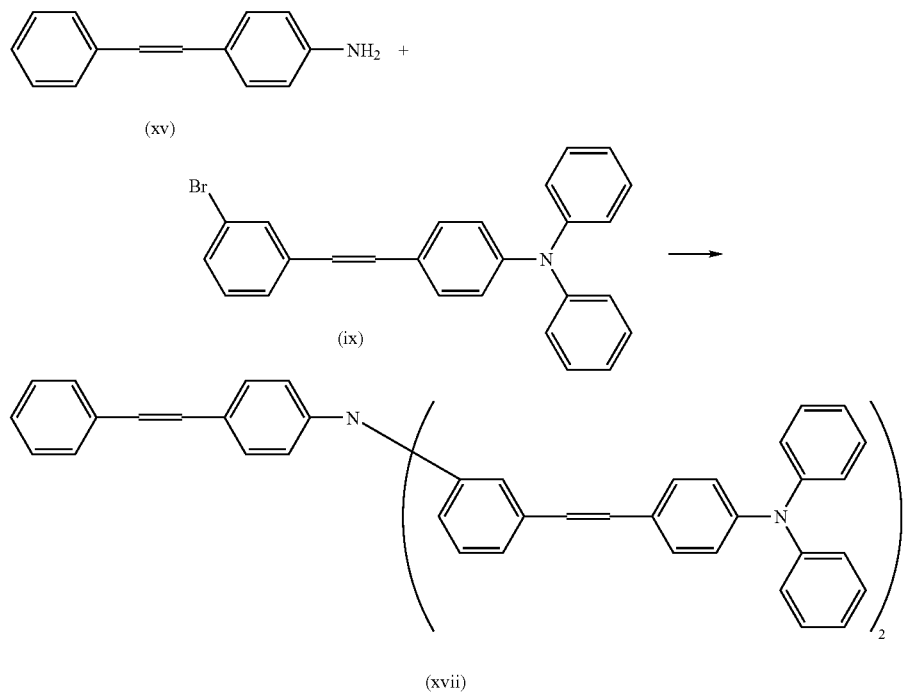

4-styrylaniline (shown by the formula (xv)), 4-(3-bromostyryl)triphenylamine (shown by the formula (ix)), copper powder and potassium carbonate were added to nitrobenzene, and they were allowed to react with one another at 200° C. for 40 hours. The mixture was purified by common method, to obtain 4-styryl-3',3"-bis-(4-diphenylaminostyryl)triphenylamine (shown by the formula (xvii)).

Example 24

Referring to FIG. 2(a), a glass substrate 11 was coated with a thin film of ITO (indium tin oxide) as the anode 12, having a resistivity of 20 Ω/□, by sputtering, the compound 1 shown by Table II -1 to a thickness of 50 nm as the hole transport layer 13 by resistance heating vacuum deposition, tris-(8-hydroxyquinolinol) aluminum (compound (a)) to a thickness of 60 nm, as the light-emitting layer 14 also by resistance heating vacuum deposition, and finally MgAg (deposition rate ratio; 10:1) to a thickness of 150 nm as the cathode 16 also by resistance heating vacuum deposition, in this order.

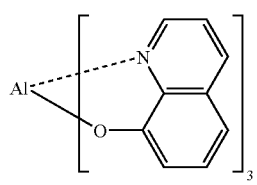

Compound (a)

Very bright green color planar-emission was performed from the light-emitting layer of tris-(8-hydroxyquinolinol) aluminum. Brightness of the light was 241 cd/m² initially at a constant current density of 10 mA/cm² in a dried nitrogen atmosphere, and 160 cd/m² after 1000 hours drive, by which is meant that this organic EL device of the present invention is more durable than those prepared by Comparative Examples 1 and 2.

Examples 25 to 29

The same procedure as used for Example 24 was repeated, except that the material applied to the bole transport layer was replaced by the compound shown by Table II-7, to prepare the organic EL devices. They emitted very bright green color emission from the light-emitting layers of tris-(8-hydroxyquinolinol) aluminum. Brightness of the emitted light, initial and after 1000 hours drive, is given in Table II-7 for each device, at a constant current density of 10 mA/cm² in a dried nitrogen atmosphere.

TABLE II-7

| Examples | Hole transport layer | Initial brightness (cd/m²) | Brightness after 1000 hours drive (cd/m²) |
|---|---|---|---|
| 25 | Compound 3 shown by Table II-1 | 232 | 166 |
| 26 | Compound 11 shown by Table II-2 | 237 | 175 |
| 27 | Compound 24 shown by Table II-4 | 254 | 192 |
| 28 | Compound 32 shown by Table II-5 | 261 | 190 |
| 29 | Compound 36 shown by Table II-5 | 225 | 169 |

Example 30

Referring to FIG. 2(b), a glass substrate 11 was coated with a thin film of ITO as the anode 12, having a resistivity of 20 Ω/□, by sputtering, the compound 1 of Table II-1 to a thickness of 40 nm as the first hole transport layer 13a by resistance heating vacuum deposition, compound (b) to a thickness of 20 nm as the second hole transport layer 13b also by resistance heating vacuum deposition, tris-(8-hydroxyquinolinol) aluminum (compound (a)) to a thickness of 50 nm as the light-emitting layer 14 also by resistance heating vacuum deposition, and finally MgAg (deposition rate ratio: 10:1) to a thickness of 150 nm as the cathode 16 also by resistance heating vacuum deposition.

Compound (b)

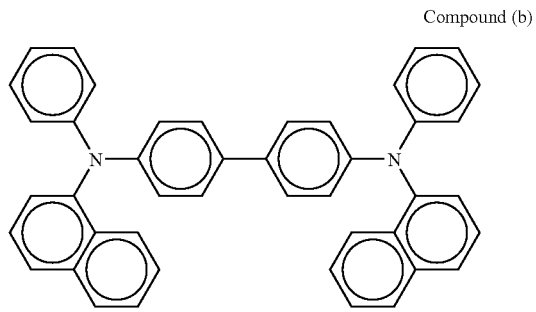

Very bright green color planar-emission was performed from the light-emitting layer of tris-(8-hydroxyquinolinol) aluminum. Brightness of the light was 294 cd/m² initially at a constant current density of 10 mA/cm² in a dried nitrogen atmosphere, and 231 cd/m² after 1000 hours drive.

Examples 31 to 35

The same procedure as used for Example 30 was repeated, except that the material applied to the first hole transport layer was replaced by the compound shown by Table II-8, to prepare the organic EL devices. They emitted very bright green color emission from the light-emitting layers of tris-(8-hydroxyquinolinol) aluminum. Brightness of the emitted light, initial and after 1000 hours drive, is given in Table II-8 for each device, at a constant current density of 10 mA/cm² in a dried nitrogen atmosphere.

TABLE II-8

| Examples | First hole transport layer | Initial brightness (cd/m²) | Brightness after 1000 hours drive (cd/m²) |
|---|---|---|---|
| 8 | Compound 3 shown by Table II-1 | 270 | 219 |
| 9 | Compound 11 shown by Table II-2 | 279 | 238 |
| 10 | Compound 24 shown by Table II-4 | 299 | 255 |
| 11 | Compound 32 shown by Table II-6 | 303 | 247 |
| 12 | Compound 36 shown by Table II-6 | 273 | 231 |

Example 36

Referring to FIG. 2(a), a glass substrate 11 was coated with a thin film of ITO as the anode 12, having a resistivity of 20 Ω/□, by sputtering. The anode 12 was coated with a solution, which was a mixture of the compound 1 of Table II-1 and polycarbonate (Mitsubishi Chemical, Z200) (1:1 by weight) dissolved in tetrahydrofuran at 1.5 wt. %, by dip coating to a thickness of 50 nm, and dried at 80° C. for 1 hour, to form the hole transport layer 13. It was then coated with tris-(8-hydroxyquinolinol) aluminum (compound (a)) to a thickness of 50 nm as the light-emitting layer 14 by resistance heating vacuum deposition, and finally MgAg (deposition rate ratio: 10:1) to a thickness of 150 nm as the cathode 16 also by resistance heating vacuum deposition.

Very bright green color planar-emission was performed from the light-emitting layer of tris-(8-hydroxyquinolinol) aluminum. Brightness of the light was 222 cd/m² initially at a constant current density of 10 mA/cm² in a dried nitrogen atmosphere, and 175 cd/m² after 1000 hours drive.

Example 37

Referring to FIG. 2(a), a glass substrate 11 was coated with a thin film of ITO as the anode 12, having a resistivity of 20 Ω/□, by sputtering. The anode 12 was coated with the compound 1 of Table II-1 and compound (b) by resistance heating vacuum deposition to a thickness of 50 nm (codeposition at a rate ratio of 7:3), to form the hole transport layer 13. It was then coated with tris-(8-hydroxyquinolinol) aluminum (compound (a)) to a thickness of 50 nm as the light-emitting layer 14 also by resistance heating vacuum deposition, and finally MgAg (deposition rate ratio: 10:1) to a thickness of 150 nm as the cathode 16 also by resistance heating vacuum deposition.

Very bright green color planar-emission was performed from the light-emitting layer of tris-(8-hydroxyquinolinol) aluminum. Brightness of the light was 262 cd/m² initially at a constant current density of 10 mA/cm² in a dried nitrogen atmosphere, and 206 cd/m² after 1000 hours drive.

Example 38

Referring to FIG. 1(a), a glass substrate 11 was coated with a thin film of ITO (indium tin oxide) as the anode 12, having a resistivity of 20 Ω/□, by sputtering, the compound 1 shown by Table II -1 to a thickness of 50 nm as the hole transport layer 13 by resistance heating vacuum deposition, tris-(8-hydroxyquinolinol) aluminum (compound (a)) and DCM (compound (c)) to a thickness of 30 nm as the light-emitting layer 14 also by resistance heating vacuum deposition (codeposition at a rate ratio of 100:2), tris-(8-hydroxyquinolinol) aluminum to a thickness of 30 nm as the electron transport layer 15 also by resistance heating vacuum deposition, and finally MgAg (deposition rate ratio: 10:1) to a thickness of 150 nm as the cathode 16 also by resistance heating vacuum deposition, in this order.

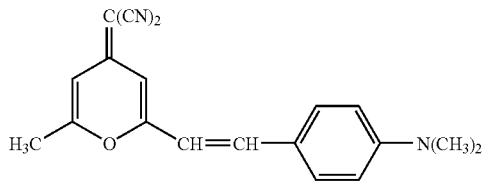

Compound (c)

Very bright orange color planar-emission was performed from the light-emitting layer of DCM. Brightness of the light was 456 cd/m$^2$ initially at a constant current density of 10 mA/cm$^2$ in a dried nitrogen atmosphere, and 324 cd/m$^2$ after 1000 hours drive.

Example 39

Referring to FIG. 4, a glass substrate 11 was coated with a thin film of ITO (indium tin oxide) as the anode 12, having a resistivity of 20 Ω/□, by sputtering, copper phthalocyanine (compound d) to a thickness of 10 nm as the anode interface layer 17 by resistance heating vacuum deposition, the compound 1 of Table II-1 to a thickness of 50 nm as the hole transport layer 13 also by resistance heating vacuum deposition, tris-(8-hydroxyquinolinol) aluminum (compound (a)) to a thickness of 50 nm as the light-emitting layer 14 also by resistance heating vacuum deposition, and finally MgAg (deposition rate ratio: 10:1) to a thickness of 150 nm as the cathode 16 also by resistance heating vacuum deposition, in this order.

Very bright green color planar-emission was performed from the light-emitting layer of tris-(8-hydroxyquinolinol) aluminum. Brightness of the light was 252 cd/m$^2$ initially at a constant current density of 10 mA/cm$^2$ in a dried nitrogen atmosphere, and 201 cd/m$^2$ after 1000 hours drive.

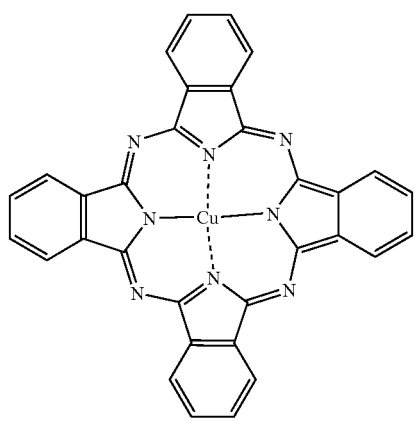

Compound (d)

Example 40

Referring to FIG. 1(*a*), a glass substrate 11 was coated with a thin film of ITO (indium tin oxide) as the anode 12, having a resistivity of 20 Ω/□, by sputtering, the compound (b) to a thickness of 50 nm as the hole transport layer 13 by resistance heating vacuum deposition, compound 1 of Table II-1 to a thickness of 50 nm as the light-emitting layer 14 also by resistance heating vacuum deposition, t-Bu-PBD (compound (e)) to a thickness of 30 nm as the electron transport layer 15 also by resistance heating vacuum deposition, and finally MgAg (deposition rate ratio: 10:1) to a thickness of 150 nm as the cathode 16 also by resistance heating vacuum deposition, in this order.

Very bright blue color planar-emission was performed from the light-emitting layer of the compound 1 shown by Table II-1. Brightness of the light was 903 cd/m$^2$ at a voltage of 8 V, by which is meant that this device has improved brightness characteristics over the one prepared by Comparative Example 3.

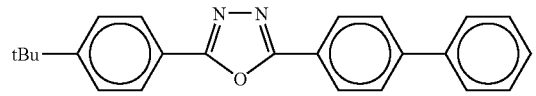

Compound (e)

Examples 41 to 45

The same procedure as used for Example 40 was repeated, except that the material applied to the light-emitting layer was replaced by the compound shown by Table II-9, to prepare the organic EL devices. They emitted very bright emission from the light-emitting layers. Brightness of the emitted light at a voltage of 8 V is given in Table II-9 for each device.

TABLE II-9

| Examples | Light-emitting layer | Brightness at 8 V (cd/m$^2$) |
| --- | --- | --- |
| 18 | Compound 3 shown by Table II-1 | 584 |
| 19 | Compound 11 shown by Table II-2 | 885 |
| 20 | Compound 24 shown by Table II-4 | 967 |
| 21 | Compound 32 shown by Table II-6 | 1002 |
| 22 | Compound 36 shown by Table II-6 | 627 |

Example 46

Referring to FIG. 1(*a*), a glass substrate 11 was coated with a thin film of ITO as the anode 12, having a resistivity of 20 Ω/□, by sputtering, and the compound (b) to a thickness of 50 nm as the hole transport layer 13 by resistance heating vacuum deposition, in this order. The hole transport layer 13 was coated with the compound 1 shown by Table II-1 and rubrene (compound (f)) to a thickness of 50 nm also by resistance heating vacuum deposition (codeposition at a rate ratio of 100:2), to form the light-emitting layer 14. It was then coated with t-Bu-PBD (compound (e)) to la thickness of 30 nm as the electron transport layer 15 also by resistance heating vacuum deposition, and finally MgAg (deposition rate ratio: 10:1) to a thickness of 150 nm as the cathode 16 also by resistance heating vacuum deposition, in this order.

Very bright yellow color planar-emission was performed from the light-emitting layer of the compound (f). Brightness of the light was 2310 cd/m² at a voltage of 8 V.

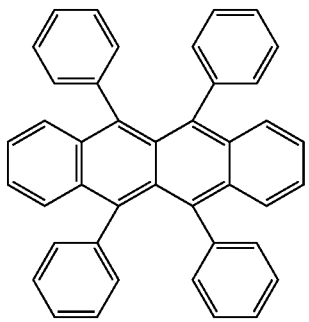

Compound (f)

Comparative Example 1

A glass substrate was coated with a thin film of ITO (indium tin oxide) as the anode, having a resistivity of 20 Ω/□, N,N'-diphenyl-N,N'-bis(3-methylphenyl)-1,1'-biphenyl-4,4'-diamine to a thickness of 50 nm as the hole transport layer, tris-(8-hydroxyquinolinol) aluminum (compound (a)) to a thickness of 60 nm as the light-emitting layer by vacuum deposition, and finally MgAg (deposition rate ratio: 10:1) to a thickness of 150 nm as the cathode also by vacuum deposition, in this order.

Very bright green color planar-emission was performed from the light-emitting layer of tris-(8-hydroxyquinolinol) aluminum. Brightness of the light was 212 cd/m² initially at a constant current density of 10 mA/cm² in a dried nitrogen atmosphere, but declined to 51 cd/m² after 630 hours drive, at which it was broken.

Comparative Example 2

A glass substrate was coated with a thin film of ITO (indium tin oxide) as the anode, having a resistivity of 20 Ω/□, by sputtering, the compound (g) to a thickness of 50 nm as the hole transport layer by resistance heating vacuum deposition, tris-(8-hydroxyquinolinol) aluminum (compound (a)) to a thickness of 60 nm as the light-emitting layer also by resistance heating vacuum deposition, and finally MgAg (deposition rate ratio: 10:1) to a thickness of 150 nm as the cathode also by resistance heating vacuum deposition, in this order.

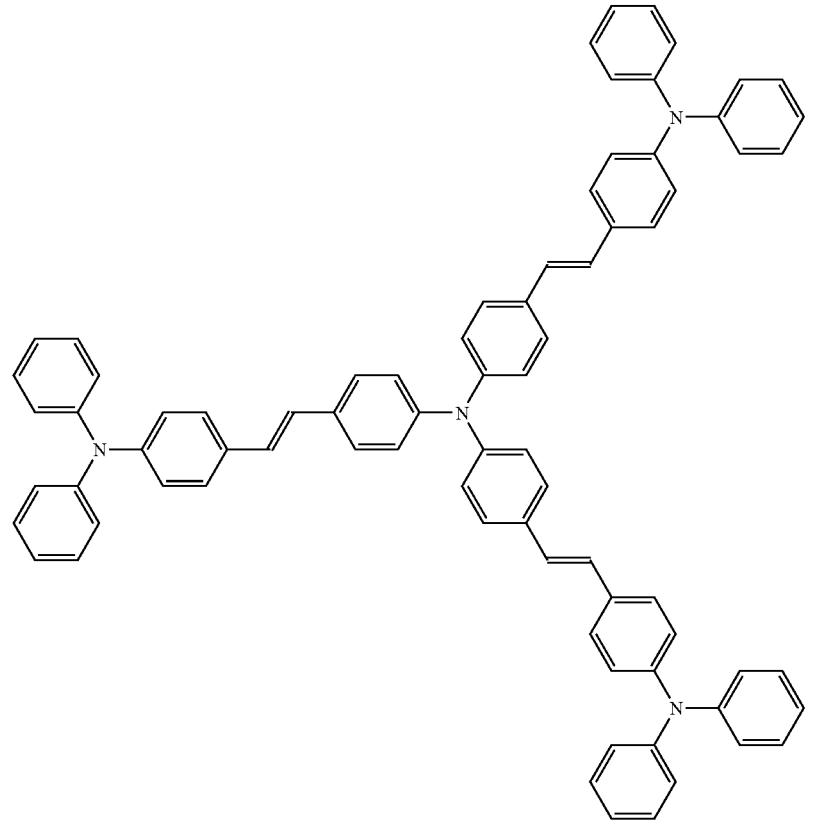

Compound (g)

Very bright green color planar-emission was performed from the light-emitting layer of tris-(8-hydroxyquinolinol) aluminum. Brightness of the light was 223 cd/m² initially at a constant current density of 10 mA/cm² in a dried nitrogen atmosphere, and 125 cd/m² after 1000 hours drive.

Comparative Example 3

A glass substrate was coated with a thin film of ITO (indium tin oxide) as the anode, having a resistivity of 20 Ω/□, by sputtering, the compound (b) to a thickness of 50 nm as the hole transport layer by resistance heating vacuum deposition, compound (g) to a thickness of 50 nm as the light-emitting layer also by resistance heating vacuum deposition, t-Bu-PBD (compound (e)) to a thickness of 30 nm as the electron transport layer also by resistance heating vacuum deposition, and finally MgAg (deposition rate-ratio: 10:1) to a thickness of 150 nm as the cathode also by resistance heating vacuum deposition, in this order.

Blue color plane-emission was performed from the light-emitting layer of the compound g. Brightness of the light was 184 cd/m² at a voltage of 8 V.

As described above, the present invention provides a durable, organic EL device emitting light of high brightness. Therefore, the present invention can provide an excellent EL material and EL device for full-color EL displays.

What is claimed is:

1. An organic electroluminescence material, comprising a compound shown by the following general formula (A-VI):

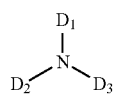

(A-VI)

wherein, $D_1$ to $D_3$, which may be the same or different, are independently, each a substituent shown by the general formula (A-VII)

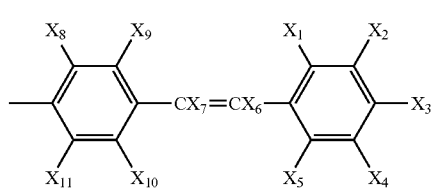

(A-VII)

wherein, at least one of $X_1$ to $X_5$ is a substituent shown by the formula —$NAr_1Ar_2$, the others being independently each a hydrogen atom, a halogen atom or hydroxyl, amino or substituted amino nitro, cyano, alkyl or substituted alkyl, alkenyl or substituted alkenyl (other than styryl), cycloalkyl or substituted cycloalkyl, alkoxy or substituted alkoxy, aromatic hydrocarbon or substituted aromatic hydrocarbon, aromatic heterocyclic or substituted aromatic heterocyclic, aralkyl or substituted aralkyl, aryloxy or substituted aryloxy, alkoxy carbonyl or substituted alkoxy carbonyl or carboxyl group; and $X_1$ to $X_5$ may form a ring by two adjacent atoms or groups;

$Ar_1$ and $Ar_2$ are independently, each an aryl group which may be substituted;

one of $X_6$ and $X_7$ is hydrogen and the other is an aromatic hydrocarbon group or an aromatic heterocyclic group, all of which may be substituted; and $X_8$ to $X_{11}$ are independently a hydrogen atom, halogen or hydroxyl, amino or substituted amino, nitro, cyano, alkyl or substituted alkyl, alkenyl or substituted alkenyl (except styryl), cycloalkyl or substituted cycloalkyl, alkoxy or substituted alkoxy, aromatic hydrocarbon or substituted aromatic hydrocarbon, aromatic heterocyclic or substituted aromatic heterocyclic, aralkyl or substituted aralkyl, aryloxy or substituted aryloxy, alkoxy carbonyl or substituted alkoxy carbonyl or carboxyl group or $X_8$ to $X_{11}$ may form a ring by two adjacent atoms or groups.

2. An organic electroluminescence material, comprising a compound shown by the following general formula (B-I):

(B-I)

wherein, $a_1$, $b_1$, and $b_2$ are independently, each an aryl group which may be substituted, $a_1$ having at least one substituent shown by the general formula (B-II), each of $b_1$ and $b_2$ having at least one substituent shown by the general formula (B-III), and $b_1$ and $b_2$ may be the same or different:

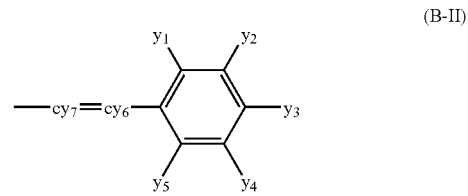

(B-II)

wherein, $y_1$ to $y_5$ are independently, each a hydrogen atom, a halogen atom or hydroxyl, nitro, cyano, alkyl or substituted alkyl, alkenyl or substituted alkenyl (except styryl), cycloalkyl or substituted cycloalkyl, alkoxy or substituted alkoxy, aromatic hydrocarbon or substituted aromatic hydrocarbon, aromatic heterocyclic or substituted aromatic heterocyclic, aralkyl or substituted aralkyl, aryloxy or substituted aryloxy, alkoxy carbonyl or substituted alkoxy carbonyl or carboxyl group; and $y_1$ to $y_5$ may form a ring by two adjacent atoms or groups;

$y_6$ and $y_7$ are independently, each a hydrogen atom, alkyl or substituted alkyl, aromatic hydrocarbon or substituted aromatic hydrocarbon, or aromatic heterocyclic or substituted aromatic heterocyclic group;

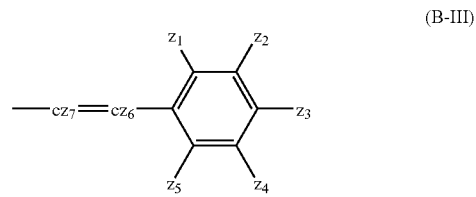

(B-III)

wherein, at least one of $z_1$ to $z_5$ is a substituent shown by the formula —$NAr_1Ar_2$, the others being independently, each a hydrogen atom, a halogen atom or hydroxyl, amino or substituted amino, nitro, cyano, alkyl or substituted alkyl, alkenyl or substituted alkenyl (except styryl), cycloalkyl or substituted cycloalkyl, alkoxy or substituted alkoxy, aromatic hydrocarbon or substituted aromatic hydrocarbon, aromatic heterocyclic or substituted aromatic heterocyclic, aralkyl or substituted aralkyl, aryloxy or substituted aryloxy, alkoxy carbonyl or substituted alkoxy carbonyl or carboxyl group; and $z_1$ to $z_5$ may form a ring by two adjacent atoms or groups;

$Ar_1$ and $Ar_2$ are independently, each an aryl group which may be substituted; and $z_6$ and $z_7$ are independently, each a hydrogen atom or alkyl or substituted alkyl, aromatic hydrocarbon or substituted aromatic hydrocarbon, or aromatic heterocyclic or substituted aromatic heterocyclic group.

3. An organic electroluminescence device comprising an anode, a hole transport region, a light emitting layer, an electron transport layer, and a cathode wherein at least one of the hole transport region, light emitting layer and electron transport layer comprises the electroluminescence material of claim 1.

4. An organic electroluminescence device comprising an anode, a hole transport region, a light emitting layer, an electron transport layer, and a cathode wherein at least one of the hole transport region, light emitting layer and electron transport layer comprises the electroluminescence material of claim 2.

5. An organic electroluminescence material comprising an organic electroluminescence material of claim 1 or claim 2 dispersed in a polymer binder.

6. An organic electroluminescence device comprising one or more layers of organic thin films placed between an anode and cathode, wherein at least one of said layers is composed of at least one organic electroluminescence material of claim 1 or claim 2.

7. The organic electroluminescence device of claim 6, wherein at least one layer composed of said at least one organic electroluminescence material is about 2 to about 500 nm thick.

8. An organic electroluminescence device of claim 6, comprising a hole transport layer, a light emitting layer and an electron transport layer, wherein at least one of the hole transport, light-emitting and electron transport layers is composed of at least one of said organic electroluminescence material.

9. The organic electroluminescence device of claim 8, wherein said light-emitting layer is doped with an organic luminescent agent.

10. The organic electroluminescence device of claim 8, wherein said hole transport layer is located between an anode and cathode and contains first and second hole transport layers facing the side of the anode and the side of the light-emitting layer, respectively, and said first hole transport layer is composed of said at least one of said organic electroluminescence material.

11. The organic electroluminescence device of claim 10, wherein said second hole transport layer contains an aromatic tertiary amine compound.

12. The organic electroluminescence device of claim 8, additionally comprising an anode interface layer located between said anode and said hole transport layer.

13. The organic electroluminescence device of claim 10, additionally comprising an anode interface layer located between said anode and said first hole transport layer.

14. The organic electroluminescence device of claim 11, additionally comprising an anode interface layer located between said anode and said first hole transport layer.

* * * * *